(12) United States Patent
Eshel et al.

(10) Patent No.: US 11,733,150 B2
(45) Date of Patent: Aug. 22, 2023

(54) DISTINGUISHING BETWEEN BLOOD SAMPLE COMPONENTS

(71) Applicant: S.D. Sight Diagnostics Ltd., Tel Aviv (IL)

(72) Inventors: Yochay Shlomo Eshel, Sde Warburg (IL); Arnon Houri Yafin, Jerusalem (IL); Joseph Joel Pollak, Neve Daniel (IL); Neta Bachar, Netanya (IL); Annael Marciano, Jerusalem (IL); Sarah Levy Schreier, Tel Aviv (IL)

(73) Assignee: S.D. Sight Diagnostics Ltd., Tel Aviv (IL)

( * ) Notice: Subject to any disclaimer, the term of this patent is extended or adjusted under 35 U.S.C. 154(b) by 502 days.

(21) Appl. No.: 16/088,321

(22) PCT Filed: Mar. 23, 2017

(86) PCT No.: PCT/IL2017/050363
§ 371 (c)(1),
(2) Date: Sep. 25, 2018

(87) PCT Pub. No.: WO2017/168411
PCT Pub. Date: Oct. 5, 2017

(65) Prior Publication Data
US 2020/0300750 A1    Sep. 24, 2020

Related U.S. Application Data

(60) Provisional application No. 62/315,223, filed on Mar. 30, 2016.

(51) Int. Cl.
*G01N 15/14* (2006.01)
*G01N 33/49* (2006.01)
(Continued)

(52) U.S. Cl.
CPC .......... *G01N 15/1475* (2013.01); *G01N 1/30* (2013.01); *G01N 33/49* (2013.01); *G02B 21/367* (2013.01);
(Continued)

(58) Field of Classification Search
CPC combination set(s) only.
See application file for complete search history.

(56) References Cited

U.S. PATENT DOCUMENTS 3,203,768 A * 8/1965 Tiller ...................... C30B 13/26
117/222
3,603,156 A   9/1971 Konkol
(Continued)

FOREIGN PATENT DOCUMENTS

CA   2655024 A    1/2008
CN   1918501 A1   2/2007
(Continued)

OTHER PUBLICATIONS

Bovik, Alan C., et. "The Essential Guide to Image Processing", Chapter 27, "Computer Assisted Microscopy" pp. 777-831; Academic Press, 2009.
(Continued)

*Primary Examiner* — Tsung Yin Tsai
(74) *Attorney, Agent, or Firm* — Sughrue Mion, PLLC

(57) ABSTRACT

Apparatus and methods are described for use with an output device (34), and a blood sample (12) that was drawn from a subject. A microscope system (10) acquires first and second images of the blood sample at respective times. A computer processor (28) determines whether, between acquisitions of the first and second images, there was relative motion between at least one erythrocyte within the sample and at least one entity within the sample, by comparing the first and second images to one another. At least (Continued)

partially in response thereto, the computer processor determines whether the entity is an extra-erythrocytic or an intra-erythrocytic entity, and generates an output on the output device, at least partially in response thereto. Other applications are also described.

28 Claims, 6 Drawing Sheets

(51) Int. Cl.
G06V 20/69 (2022.01)
G01N 1/30 (2006.01)
G02B 21/36 (2006.01)
G01N 15/10 (2006.01)

(52) U.S. Cl.
CPC .... G01N 2015/1006 (2013.01); G06V 20/698 (2022.01)

(56) References Cited

U.S. PATENT DOCUMENTS

| | | | |
|---|---|---|---|
| 3,676,076 | A | 7/1972 | Grady |
| 3,786,184 | A | 1/1974 | Pieters |
| 3,916,205 | A | 10/1975 | Kleinerman |
| 3,967,056 | A | 6/1976 | Yata et al. |
| 4,030,888 | A | 6/1977 | Yamamoto |
| 4,076,419 | A | 2/1978 | Kleker |
| 4,097,845 | A * | 6/1978 | Bacus .......... G06V 20/69 382/226 |
| 4,199,748 | A * | 4/1980 | Bacus .......... G06V 20/69 377/10 |
| 4,209,548 | A | 6/1980 | Bacus |
| 4,350,884 | A | 9/1982 | Dieter |
| 4,453,266 | A | 6/1984 | Bacus |
| 4,454,235 | A | 6/1984 | Johnson |
| 4,494,479 | A | 1/1985 | Brury et al. |
| 4,580,895 | A | 4/1986 | Patel |
| 4,700,298 | A | 10/1987 | Palcic et al. |
| 4,761,381 | A | 8/1988 | Blatt et al. |
| 4,774,192 | A | 9/1988 | Terminiello et al. |
| 4,803,352 | A | 2/1989 | Bierleutgeb |
| 4,849,340 | A | 7/1989 | Oberhardt |
| 4,849,430 | A | 7/1989 | Fleet et al. |
| 4,851,330 | A | 7/1989 | Kohne |
| 4,902,101 | A | 2/1990 | Fujihara et al. |
| 5,001,067 | A | 3/1991 | Coleman et al. |
| 5,064,282 | A | 11/1991 | Curtis |
| 5,229,265 | A | 7/1993 | Tometsko |
| 5,300,779 | A | 4/1994 | Hillman et al. |
| 5,331,958 | A | 7/1994 | Oppenheimer |
| 5,430,542 | A | 7/1995 | Shepherd et al. |
| 5,470,751 | A | 11/1995 | Sakata et al. |
| 5,566,249 | A | 10/1996 | Rosenlof et al. |
| 5,625,706 | A | 4/1997 | Lee et al. |
| 5,663,057 | A | 9/1997 | Drocourt et al. |
| 5,671,288 | A | 9/1997 | Wilhelm et al. |
| 5,672,861 | A | 9/1997 | Fairley et al. |
| 5,674,457 | A | 10/1997 | Williamsson et al. |
| 5,745,804 | A | 4/1998 | Iwane |
| 5,782,770 | A | 7/1998 | Mooradian et al. |
| 5,827,190 | A | 10/1998 | Palcic et al. |
| 5,834,217 | A | 11/1998 | Levine et al. |
| 5,932,872 | A | 8/1999 | Price |
| 5,948,686 | A | 9/1999 | Wardlaw |
| 5,978,497 | A | 11/1999 | Lee et al. |
| 5,985,595 | A | 11/1999 | Krider |
| 6,005,964 | A | 12/1999 | Reid et al. |
| 6,027,695 | A | 2/2000 | Oldenburg et al. |
| 6,064,474 | A | 5/2000 | Lee et al. |
| 6,074,879 | A | 6/2000 | Zelmanovic et al. |
| 6,101,404 | A | 8/2000 | Yoon et al. |
| 6,235,536 | B1 | 5/2001 | Wardlaw |
| 6,262,798 | B1 | 7/2001 | Shepherd et al. |
| 6,320,979 | B1 | 11/2001 | Melen |
| 6,330,348 | B1 | 12/2001 | Kerschmann et al. |
| 6,339,472 | B1 * | 1/2002 | Hafeman .......... G01N 21/6452 356/436 |
| 6,350,131 | B1 | 2/2002 | Shih |
| 6,350,613 | B1 | 2/2002 | Wardlaw et al. |
| 6,448,024 | B1 | 9/2002 | Bruegger |
| 6,519,355 | B2 | 2/2003 | Nelson |
| 6,554,788 | B1 | 4/2003 | Hunley et al. |
| 6,555,421 | B2 | 4/2003 | Matsuyama et al. |
| 6,582,964 | B1 | 6/2003 | Samsoondar et al. |
| 6,611,777 | B2 | 8/2003 | Samsoondar |
| 6,632,681 | B1 | 10/2003 | Chu |
| 6,658,143 | B2 | 12/2003 | Hansen et al. |
| 6,664,528 | B1 | 12/2003 | Cartlidge et al. |
| 6,711,516 | B2 | 3/2004 | Samsoondar |
| 6,799,119 | B1 | 9/2004 | Voorhees et al. |
| 6,819,408 | B1 | 11/2004 | Scrivens et al. |
| 6,831,733 | B2 | 12/2004 | Pettersson et al. |
| 6,834,237 | B2 | 12/2004 | Noergaard et al. |
| 6,836,559 | B2 | 12/2004 | Abdel-Fattah et al. |
| 6,842,233 | B2 | 1/2005 | Narisada et al. |
| 6,866,823 | B2 | 3/2005 | Wardlaw |
| 6,872,930 | B2 | 3/2005 | Cartlidge et al. |
| 6,898,451 | B2 | 5/2005 | Wuori |
| 6,903,323 | B2 | 6/2005 | Cartlidge et al. |
| 6,929,953 | B1 | 8/2005 | Wardlaw |
| 6,949,384 | B2 | 9/2005 | Samsoondar |
| 6,955,872 | B2 | 10/2005 | Maples et al. |
| 6,956,650 | B2 | 10/2005 | Boas et al. |
| 6,989,891 | B2 | 1/2006 | Braig et al. |
| 7,027,628 | B1 | 4/2006 | Gagnon et al. |
| 7,030,351 | B2 | 4/2006 | Wasserman et al. |
| 7,034,883 | B1 | 4/2006 | Rosenqvist |
| 7,105,795 | B2 | 9/2006 | Cartlidge et al. |
| 7,132,636 | B1 | 11/2006 | Cartlidge et al. |
| 7,133,547 | B2 | 11/2006 | Marcelpoil et al. |
| 7,151,246 | B2 | 12/2006 | Fein et al. |
| 7,155,049 | B2 | 12/2006 | Wetzel et al. |
| 7,248,716 | B2 | 7/2007 | Fein et al. |
| 7,274,810 | B2 | 9/2007 | Reeves et al. |
| 7,283,217 | B2 | 10/2007 | Ikeuchi et al. |
| 7,288,751 | B2 | 10/2007 | Cartlidge et al. |
| 7,305,109 | B1 | 12/2007 | Gagnon et al. |
| 7,324,694 | B2 | 1/2008 | Chapoulaud et al. |
| 7,329,537 | B2 | 2/2008 | Qiu |
| 7,338,168 | B2 | 3/2008 | Cartlidge et al. |
| 7,344,890 | B2 | 3/2008 | Perez et al. |
| 7,346,205 | B2 | 3/2008 | Walker, Jr. |
| 7,369,696 | B2 | 5/2008 | Arini et al. |
| 7,385,168 | B2 | 6/2008 | Cartlidge et al. |
| 7,387,898 | B1 | 6/2008 | Gordon |
| 7,411,680 | B2 | 8/2008 | Chang et al. |
| 7,417,213 | B2 | 8/2008 | Krief et al. |
| 7,425,421 | B2 | 9/2008 | Dertinger |
| 7,439,478 | B2 | 10/2008 | Cartlidge et al. |
| 7,450,223 | B2 | 11/2008 | Ikeuchi et al. |
| 7,450,762 | B2 | 11/2008 | Morell |
| 7,460,222 | B2 | 12/2008 | Kalveram et al. |
| 7,490,085 | B2 | 2/2009 | Walker et al. |
| 7,493,219 | B1 | 2/2009 | Qi et al. |
| 7,580,120 | B2 | 8/2009 | Hamada et al. |
| 7,599,893 | B2 | 10/2009 | Sapir et al. |
| 7,601,938 | B2 | 10/2009 | Cartlidge et al. |
| 7,602,954 | B2 | 10/2009 | Marcelpoil et al. |
| 7,605,356 | B2 | 10/2009 | Krief et al. |
| 7,609,369 | B2 | 10/2009 | Simon-Lopez |
| 7,630,063 | B2 | 12/2009 | Padmanabhan et al. |
| 7,633,604 | B2 | 12/2009 | Ikeuchi et al. |
| 7,638,748 | B2 | 12/2009 | Krief et al. |
| 7,663,738 | B2 | 2/2010 | Johansson |
| 7,668,362 | B2 | 2/2010 | Olson et al. |
| 7,692,131 | B2 | 4/2010 | Fein et al. |
| 7,697,764 | B2 | 4/2010 | Kataoka |
| 7,702,181 | B2 | 4/2010 | Gouch |
| 7,706,862 | B2 | 4/2010 | Alfano et al. |
| 7,713,474 | B2 | 5/2010 | Schulman et al. |
| 7,747,153 | B2 | 6/2010 | Ibaraki |
| 7,765,069 | B2 | 6/2010 | Ostoich et al. |

(56) References Cited

U.S. PATENT DOCUMENTS

| | | | |
|---|---|---|---|
| 7,777,869 B2 | 8/2010 | Nerin et al. | |
| 7,787,109 B2 | 8/2010 | Dosmann et al. | |
| 7,796,797 B2 * | 9/2010 | Nakaya | G01N 15/147 382/134 |
| 7,863,552 B2 | 1/2011 | Cartlidge et al. | |
| 7,869,009 B2 | 1/2011 | Dosmann et al. | |
| 7,894,047 B2 | 2/2011 | Hamada et al. | |
| 7,911,617 B2 | 3/2011 | Padmanabhan et al. | |
| 7,925,070 B2 | 4/2011 | Sumida et al. | |
| 7,929,121 B2 | 4/2011 | Wardlaw et al. | |
| 7,933,435 B2 | 4/2011 | Hunter et al. | |
| 7,936,913 B2 | 5/2011 | Nordell et al. | |
| 7,951,599 B2 | 5/2011 | Levine et al. | |
| 7,995,200 B2 | 8/2011 | Matsumoto | |
| 7,998,435 B2 | 8/2011 | Reed | |
| 8,000,511 B2 | 8/2011 | Perz | |
| 8,044,974 B2 | 10/2011 | Sumida et al. | |
| 8,045,782 B2 | 10/2011 | Li et al. | |
| 8,055,471 B2 | 11/2011 | Qi et al. | |
| 8,064,680 B2 | 11/2011 | Ramoser et al. | |
| 8,077,296 B2 | 12/2011 | Wardlaw et al. | |
| 8,081,303 B2 | 12/2011 | Levine et al. | |
| 8,105,554 B2 | 1/2012 | Kanigan et al. | |
| 8,125,643 B2 | 2/2012 | Hansen | |
| 8,131,035 B2 | 3/2012 | Grady et al. | |
| 8,131,052 B2 | 3/2012 | Alexandrov | |
| 8,150,114 B2 | 4/2012 | Svanberg et al. | |
| 8,154,713 B2 | 4/2012 | Simon-Lopez | |
| 8,165,385 B2 | 4/2012 | Reeves et al. | |
| 8,175,353 B2 | 5/2012 | Westphal et al. | |
| 8,179,597 B2 * | 5/2012 | Namba | G02B 21/0088 359/383 |
| 8,184,273 B2 | 5/2012 | Dosmann et al. | |
| 8,192,995 B2 | 6/2012 | Zhang et al. | |
| 8,216,832 B2 | 7/2012 | Battrell et al. | |
| 8,224,058 B2 | 7/2012 | Lindberg et al. | |
| 8,269,954 B2 | 9/2012 | Levine et al. | |
| 8,280,134 B2 | 10/2012 | Hoyt | |
| 8,310,659 B2 | 11/2012 | Wardlaw et al. | |
| 8,320,655 B2 | 11/2012 | Sarachan et al. | |
| 8,327,724 B2 * | 12/2012 | Fairs | B01L 3/502 73/863 |
| 8,331,642 B2 | 12/2012 | Zerfass et al. | |
| 8,339,586 B2 | 12/2012 | Zahniser et al. | |
| 8,345,227 B2 | 1/2013 | Zahniser et al. | |
| 8,351,676 B2 | 1/2013 | Dai et al. | |
| 8,363,221 B2 | 1/2013 | Hansen et al. | |
| 8,379,944 B2 | 2/2013 | Grady et al. | |
| 8,406,498 B2 * | 3/2013 | Ortyn | G06V 20/695 382/133 |
| 8,428,331 B2 | 4/2013 | DiMarzio et al. | |
| 8,432,392 B2 | 4/2013 | Kim et al. | |
| 8,477,294 B2 | 7/2013 | Zahniser et al. | |
| 8,481,303 B2 | 7/2013 | Faris et al. | |
| 8,488,111 B2 | 7/2013 | Zahniser et al. | |
| 8,491,499 B2 | 7/2013 | Choi et al. | |
| 8,526,704 B2 | 9/2013 | Dobbe | |
| 8,570,496 B2 | 10/2013 | Chen | |
| 8,582,924 B2 | 11/2013 | De La Torre-Bueno et al. | |
| 8,638,427 B2 | 1/2014 | Wardlaw et al. | |
| 8,712,142 B2 | 4/2014 | Rajpoot et al. | |
| 8,736,824 B2 | 5/2014 | Matsui et al. | |
| 8,744,165 B2 | 6/2014 | Liu et al. | |
| 8,778,687 B2 | 7/2014 | Levine et al. | |
| 8,787,650 B2 | 7/2014 | Muragame | |
| 8,792,693 B2 | 7/2014 | Satish et al. | |
| 8,831,733 B2 | 9/2014 | Wilke et al. | |
| 8,837,803 B2 | 9/2014 | Wang et al. | |
| 8,849,024 B2 | 9/2014 | Shinoda et al. | |
| 8,873,827 B2 | 10/2014 | McCulloch et al. | |
| 8,877,458 B2 | 11/2014 | Maurer | |
| 8,878,923 B2 | 11/2014 | Henderson et al. | |
| 8,885,154 B2 | 11/2014 | Wardlaw et al. | |
| 8,885,912 B2 | 11/2014 | Sui | |
| 8,891,851 B2 | 11/2014 | Spaulding | |
| 8,922,761 B2 | 12/2014 | Zahniser et al. | |
| 8,942,458 B2 | 1/2015 | Takahashi et al. | |
| 8,964,171 B2 | 2/2015 | Zahniser et al. | |
| 8,992,750 B1 | 3/2015 | Beaty | |
| 8,994,930 B2 | 3/2015 | Levine et al. | |
| 9,012,868 B2 | 4/2015 | Courtney et al. | |
| 9,041,792 B2 | 5/2015 | Van Leeuwen et al. | |
| 9,046,473 B2 | 6/2015 | Levine et al. | |
| 9,050,595 B2 | 6/2015 | Miller et al. | |
| 9,064,301 B2 | 6/2015 | Zie et al. | |
| 9,176,121 B2 | 11/2015 | Winkelman et al. | |
| 9,186,843 B2 | 11/2015 | Chan et al. | |
| 9,240,043 B2 | 1/2016 | Christiansen et al. | |
| 9,322,767 B2 | 4/2016 | Ehrenkranz | |
| 9,329,129 B2 * | 5/2016 | Pollak | G01N 1/38 |
| 9,342,734 B2 | 5/2016 | Lin et al. | |
| 9,404,852 B2 | 8/2016 | Braig et al. | |
| 9,470,609 B2 | 10/2016 | Wimberger-Friedl et al. | |
| 9,477,875 B2 | 10/2016 | Ohya et al. | |
| 9,522,396 B2 * | 12/2016 | Bachelet | B01L 3/502715 |
| 9,528,978 B2 | 12/2016 | Yamada | |
| 9,588,033 B2 | 3/2017 | Zahniser et al. | |
| 9,767,343 B1 | 9/2017 | Jones et al. | |
| 9,820,990 B2 | 11/2017 | Pak et al. | |
| 9,933,363 B2 * | 4/2018 | Danuser | G06T 3/4053 |
| 9,934,571 B2 | 4/2018 | Ozaki et al. | |
| 9,976,945 B2 | 5/2018 | Kendall et al. | |
| 10,024,858 B2 | 7/2018 | Smith et al. | |
| 10,061,972 B2 | 8/2018 | Champlin et al. | |
| 10,093,957 B2 * | 10/2018 | Pollak | G01N 15/1475 |
| 10,169,861 B2 | 1/2019 | Ozaki et al. | |
| 10,176,565 B2 | 1/2019 | Greenfield et al. | |
| 10,281,386 B2 | 5/2019 | Hsu et al. | |
| 10,482,595 B2 | 11/2019 | Yorav-Raphael et al. | |
| 10,488,644 B2 * | 11/2019 | Eshel | G01N 21/8851 |
| 10,508,983 B2 | 12/2019 | Kendall et al. | |
| 10,640,807 B2 | 5/2020 | Pollak et al. | |
| 10,663,712 B2 * | 5/2020 | Eshel | G01N 21/8851 |
| 10,843,190 B2 * | 11/2020 | Bachelet | G01N 21/6458 |
| 11,199,690 B2 | 12/2021 | Eshel et al. | |
| 2002/0009711 A1 | 1/2002 | Wada et al. | |
| 2002/0028158 A1 | 3/2002 | Wardlaw | |
| 2002/0028471 A1 | 5/2002 | Oberhardt | |
| 2003/0017085 A1 | 1/2003 | Kercso et al. | |
| 2003/0161514 A1 | 8/2003 | Curry | |
| 2003/0170613 A1 | 9/2003 | Straus | |
| 2003/0197925 A1 | 10/2003 | Hamborg | |
| 2003/0224522 A1 | 12/2003 | de Jong et al. | |
| 2003/0227612 A1 | 12/2003 | Fein et al. | |
| 2003/0227673 A1 | 12/2003 | Nakagawa | |
| 2003/0231791 A1 | 12/2003 | Torre-Bueno et al. | |
| 2003/0231971 A1 | 12/2003 | Torre-Bueno et al. | |
| 2004/0122216 A1 * | 6/2004 | Nielsen | C07K 14/505 530/351 |
| 2004/0132171 A1 | 7/2004 | Rule et al. | |
| 2004/0170312 A1 | 9/2004 | Soenksen | |
| 2004/0185447 A1 | 9/2004 | Maples et al. | |
| 2004/0218804 A1 | 11/2004 | Affleck et al. | |
| 2004/0240050 A1 | 12/2004 | Ogihara | |
| 2004/0241677 A1 * | 12/2004 | Lin | G01N 15/1475 435/6.12 |
| 2005/0089208 A1 * | 4/2005 | Dong | G06T 3/4038 382/133 |
| 2005/0109959 A1 | 5/2005 | Wasserman et al. | |
| 2005/0175992 A1 | 8/2005 | Aberl et al. | |
| 2005/0286800 A1 | 12/2005 | Gouch | |
| 2006/0002817 A1 | 1/2006 | Bohm et al. | |
| 2006/0003458 A1 | 1/2006 | Golovchenko et al. | |
| 2006/0045505 A1 | 3/2006 | Zeineh et al. | |
| 2006/0051778 A1 * | 3/2006 | Kallick | G01N 33/564 435/6.12 |
| 2006/0063185 A1 | 3/2006 | Vannier | |
| 2006/0187442 A1 | 8/2006 | Chang et al. | |
| 2006/0190226 A1 | 8/2006 | Jojic et al. | |
| 2006/0222567 A1 | 10/2006 | Kloepfer et al. | |
| 2006/0223052 A1 | 10/2006 | MacDonald et al. | |
| 2006/0223165 A1 | 10/2006 | Chang et al. | |
| 2007/0054350 A1 | 3/2007 | Walker | |

(56) References Cited

U.S. PATENT DOCUMENTS

| | | |
|---|---|---|
| 2007/0076190 A1* | 4/2007 | Nakaya .............. G01N 15/1475 382/134 |
| 2007/0161075 A1 | 7/2007 | Gleich |
| 2007/0172956 A1 | 7/2007 | Magari et al. |
| 2007/0243117 A1 | 10/2007 | Wardlaw |
| 2007/0250301 A1 | 10/2007 | Vaisberg et al. |
| 2007/0252984 A1 | 11/2007 | Van Beek et al. |
| 2008/0019584 A1 | 1/2008 | Lindberg et al. |
| 2008/0020128 A1 | 1/2008 | van Ryper et al. |
| 2008/0059135 A1 | 3/2008 | Murugkar et al. |
| 2008/0118399 A1 | 5/2008 | Fleming |
| 2008/0187466 A1 | 8/2008 | Wardlaw |
| 2008/0212069 A1 | 9/2008 | Goldberg et al. |
| 2008/0260369 A1 | 10/2008 | Ibaraki |
| 2008/0273776 A1 | 11/2008 | Krief et al. |
| 2008/0305514 A1 | 12/2008 | Alford et al. |
| 2009/0066934 A1 | 3/2009 | Gao et al. |
| 2009/0074282 A1 | 3/2009 | Pinard et al. |
| 2009/0075324 A1 | 3/2009 | Pettersson |
| 2009/0086314 A1* | 4/2009 | Namba ............... G02B 21/34 359/383 |
| 2009/0128618 A1 | 5/2009 | Fahn et al. |
| 2009/0185734 A1 | 7/2009 | Lindberg et al. |
| 2009/0191098 A1 | 7/2009 | Beard et al. |
| 2009/0195688 A1 | 8/2009 | Henderson et al. |
| 2009/0213214 A1 | 8/2009 | Yamada |
| 2009/0258347 A1 | 10/2009 | Scott |
| 2009/0269799 A1 | 10/2009 | Winkelman et al. |
| 2009/0291854 A1 | 11/2009 | Wiesinger-Mayr et al. |
| 2010/0003265 A1 | 1/2010 | Scheffler et al. |
| 2010/0068747 A1 | 3/2010 | Herrenknecht |
| 2010/0104169 A1 | 4/2010 | Yamada |
| 2010/0112631 A1 | 5/2010 | Hur et al. |
| 2010/0120129 A1 | 5/2010 | Amshey et al. |
| 2010/0136556 A1 | 6/2010 | Friedberger et al. |
| 2010/0136570 A1 | 6/2010 | Goldberg et al. |
| 2010/0152054 A1 | 6/2010 | Love et al. |
| 2010/0157086 A1 | 6/2010 | Segale et al. |
| 2010/0172020 A1 | 7/2010 | Price et al. |
| 2010/0192706 A1* | 8/2010 | Fairs ................... B01L 3/502 73/863.23 |
| 2010/0232675 A1* | 9/2010 | Ortyn .................. G06V 20/695 382/134 |
| 2010/0234703 A1* | 9/2010 | Sterling ........... A61B 5/150992 600/310 |
| 2010/0253907 A1* | 10/2010 | Korb ..................... A61B 3/14 351/206 |
| 2010/0254596 A1 | 10/2010 | Xiong et al. |
| 2010/0256918 A1 | 10/2010 | Chen et al. |
| 2010/0265323 A1 | 10/2010 | Perz |
| 2010/0272334 A1* | 10/2010 | Yamada ................ G01N 1/312 382/128 |
| 2010/0295998 A1 | 11/2010 | Sakai et al. |
| 2010/0300563 A1 | 12/2010 | Ramunas et al. |
| 2011/0007178 A1 | 1/2011 | Kahlman |
| 2011/0009163 A1 | 1/2011 | Fletcher et al. |
| 2011/0030458 A1 | 2/2011 | Park et al. |
| 2011/0059481 A1 | 3/2011 | Wardlaw et al. |
| 2011/0102571 A1 | 5/2011 | Yoneyama |
| 2011/0123398 A1 | 5/2011 | Carrilho et al. |
| 2011/0144480 A1 | 6/2011 | Lu et al. |
| 2011/0149097 A1 | 6/2011 | Danuser et al. |
| 2011/0151502 A1 | 6/2011 | Kendall et al. |
| 2011/0178716 A1 | 7/2011 | Krockenberger et al. |
| 2011/0212486 A1 | 9/2011 | Yamada et al. |
| 2011/0243794 A1 | 10/2011 | Wardlaw |
| 2011/0249910 A1 | 10/2011 | Henderson et al. |
| 2011/0275111 A1 | 11/2011 | Pettigrew et al. |
| 2011/0301012 A1 | 12/2011 | Dolecek et al. |
| 2012/0002195 A1 | 1/2012 | Wu et al. |
| 2012/0021951 A1 | 1/2012 | Hess et al. |
| 2012/0030618 A1 | 2/2012 | Leong et al. |
| 2012/0044342 A1 | 2/2012 | Hing et al. |
| 2012/0058504 A1 | 3/2012 | Li et al. |
| 2012/0092477 A1 | 4/2012 | Kawano et al. |
| 2012/0120221 A1 | 5/2012 | Dong et al. |
| 2012/0169863 A1* | 7/2012 | Bachelet ................ G01N 21/23 348/79 |
| 2012/0225446 A1 | 9/2012 | Wimberger-Friedl et al. |
| 2012/0237107 A1 | 9/2012 | Tawfik et al. |
| 2012/0275671 A1 | 11/2012 | Eichhorn et al. |
| 2012/0312957 A1 | 12/2012 | Loney et al. |
| 2012/0320045 A1 | 12/2012 | Yao et al. |
| 2013/0023007 A1 | 1/2013 | Zahniser et al. |
| 2013/0078668 A1 | 3/2013 | Levine et al. |
| 2013/0130262 A1 | 5/2013 | Battrell et al. |
| 2013/0169948 A1 | 7/2013 | Xie et al. |
| 2013/0170730 A1 | 7/2013 | Yu et al. |
| 2013/0176551 A1 | 7/2013 | Wardlaw et al. |
| 2013/0177974 A1 | 7/2013 | Mamghani et al. |
| 2013/0203082 A1 | 8/2013 | Gonda et al. |
| 2013/0273968 A1 | 10/2013 | Rhoads et al. |
| 2013/0284924 A1 | 10/2013 | Mizuochi et al. |
| 2013/0290225 A1 | 10/2013 | Kamath et al. |
| 2013/0323757 A1 | 12/2013 | Poher |
| 2014/0139625 A1 | 5/2014 | Mathuis et al. |
| 2014/0139630 A1 | 5/2014 | Kowalevicz |
| 2014/0185906 A1 | 7/2014 | Ding et al. |
| 2014/0186859 A1 | 7/2014 | Calderwood et al. |
| 2014/0205176 A1 | 7/2014 | Obrien et al. |
| 2014/0270425 A1 | 9/2014 | Kenny et al. |
| 2014/0347459 A1* | 11/2014 | Greenfield ............ G02B 21/367 382/133 |
| 2014/0347463 A1 | 11/2014 | Lin |
| 2014/0353524 A1* | 12/2014 | Danuser ................ G06T 3/4053 250/459.1 |
| 2015/0037806 A1 | 2/2015 | Pollak |
| 2015/0124082 A1* | 5/2015 | Kato .................... G06V 20/693 348/135 |
| 2015/0190063 A1* | 7/2015 | Zakharov ............ A61B 5/14551 600/479 |
| 2015/0246170 A1* | 9/2015 | Miao .................... A61M 1/3679 210/663 |
| 2015/0278575 A1 | 10/2015 | Allano et al. |
| 2015/0302237 A1 | 10/2015 | Ohya et al. |
| 2015/0316477 A1 | 11/2015 | Pollak et al. |
| 2016/0042507 A1 | 2/2016 | Turner |
| 2016/0187235 A1 | 6/2016 | Fine |
| 2016/0208306 A1 | 7/2016 | Pollak et al. |
| 2016/0246046 A1 | 8/2016 | Yorav Raphael et al. |
| 2016/0250312 A1* | 9/2016 | Longley ............... A61K 39/015 424/199.1 |
| 2016/0279633 A1* | 9/2016 | Bachelet ............ G01N 21/6458 |
| 2017/0052110 A1 | 2/2017 | Malissek et al. |
| 2017/0115271 A1 | 4/2017 | Xie et al. |
| 2017/0160185 A1 | 6/2017 | Minemura et al. |
| 2017/0191945 A1 | 7/2017 | Zhang et al. |
| 2017/0218425 A1 | 8/2017 | Chen et al. |
| 2017/0292905 A1 | 10/2017 | Obrien et al. |
| 2017/0307496 A1 | 10/2017 | Zahniser et al. |
| 2017/0326549 A1 | 11/2017 | Jones et al. |
| 2017/0328924 A1 | 11/2017 | Jones et al. |
| 2018/0246313 A1* | 8/2018 | Eshel ................... G02B 21/365 |
| 2018/0296102 A1 | 10/2018 | Satish et al. |
| 2018/0297024 A1 | 10/2018 | Tran |
| 2019/0002950 A1 | 1/2019 | Pollak et al. |
| 2019/0087953 A1 | 3/2019 | Yorav-Raphael et al. |
| 2019/0130567 A1 | 5/2019 | Greenfield et al. |
| 2019/0145963 A1 | 5/2019 | Zait et al. |
| 2019/0302099 A1 | 10/2019 | Pollak et al. |
| 2019/0347467 A1 | 11/2019 | Ohsaka et al. |
| 2020/0034967 A1 | 1/2020 | Yorav-Raphael et al. |
| 2020/0049970 A1 | 2/2020 | Eshel et al. |
| 2020/0111209 A1 | 4/2020 | Greenfield et al. |
| 2020/0249458 A1 | 8/2020 | Eshel et al. |

FOREIGN PATENT DOCUMENTS

| | | |
|---|---|---|
| CN | 101403650 A | 4/2009 |
| CN | 101501785 A | 8/2009 |
| CN | 102282467 A | 12/2011 |
| EP | 0073551 A2 | 3/1983 |

(56) References Cited

FOREIGN PATENT DOCUMENTS

| | | |
|---|---|---|
| EP | 0479231 A1 | 4/1992 |
| EP | 1 381 229 A1 | 1/2004 |
| EP | 1698883 A1 | 9/2006 |
| EP | 2145684 A2 | 1/2010 |
| EP | 2211165 A2 | 7/2010 |
| EP | 3001174 A1 | 3/2016 |
| EP | 3 123 927 A1 | 2/2017 |
| EP | 3482189 A1 | 5/2019 |
| EP | 1 873 232 B1 | 2/2020 |
| GB | 2329014 A | 3/1999 |
| JP | 60-162955 A | 8/1985 |
| JP | 61-198204 A | 9/1986 |
| JP | H08-313340 A | 11/1996 |
| JP | 9-54083 A | 2/1997 |
| JP | H11-73903 A | 3/1999 |
| JP | 2000-199845 A | 7/2000 |
| JP | 2002-516982 A | 6/2002 |
| JP | 2004-144526 A | 5/2004 |
| JP | 2004-257768 A | 9/2004 |
| JP | 2006-506607 A | 2/2006 |
| JP | 2006-301270 A | 11/2006 |
| JP | 2007-40814 A | 2/2007 |
| JP | 2009-180539 A | 8/2009 |
| JP | 2009-233927 A | 10/2009 |
| JP | 2009-268432 A | 11/2009 |
| JP | 2011-95225 A | 5/2011 |
| JP | 2013-515264 A | 5/2013 |
| JP | 2013-541767 A | 11/2013 |
| JP | 2014-41139 A | 3/2014 |
| JP | 2015-57600 A | 3/2015 |
| JP | 2016-70658 A | 5/2016 |
| JP | 2017-209530 A | 11/2017 |
| JP | 2018-525611 A | 9/2018 |
| RU | 2402006 C1 | 10/2010 |
| WO | 85/05446 A1 | 12/1985 |
| WO | 96/01438 A1 | 1/1996 |
| WO | 96/12981 A1 | 5/1996 |
| WO | 96/13615 A1 | 5/1996 |
| WO | 00/06765 A1 | 2/2000 |
| WO | 00/52195 A1 | 9/2000 |
| WO | 00/55572 A1 | 9/2000 |
| WO | 03/056327 A1 | 7/2003 |
| WO | 2003/065358 A2 | 8/2003 |
| WO | 03/073365 A1 | 9/2003 |
| WO | 03/081525 A1 | 10/2003 |
| WO | 2004/020112 | 3/2004 |
| WO | 2004/111610 A2 | 12/2004 |
| WO | 2005/121863 A1 | 12/2005 |
| WO | 2006/121266 A1 | 11/2006 |
| WO | 2008/063135 A1 | 5/2008 |
| WO | 2010/036827 A1 | 4/2010 |
| WO | 2010/056740 A1 | 5/2010 |
| WO | 2010/116341 A1 | 10/2010 |
| WO | 2010/126903 A1 | 11/2010 |
| WO | 2010/137543 A1 | 12/2010 |
| WO | 2011/056658 A1 | 5/2011 |
| WO | 2011/076413 A1 | 6/2011 |
| WO | 2011/123070 A1 | 10/2011 |
| WO | 2011/143075 A2 | 11/2011 |
| WO | 2012/000102 A1 | 1/2012 |
| WO | 2012/029269 A1 | 3/2012 |
| WO | 2012/030313 A1 | 3/2012 |
| WO | 2012/090198 A2 | 7/2012 |
| WO | 2012/154333 A1 | 11/2012 |
| WO | 2013/041951 A1 | 3/2013 |
| WO | 2013/098821 A1 | 7/2013 |
| WO | 2014/159620 A1 | 10/2014 |
| WO | 2014/188405 A1 | 11/2014 |
| WO | 2015/001553 A1 | 1/2015 |
| WO | 2015/029032 A1 | 3/2015 |
| WO | 2015/089632 A1 | 6/2015 |
| WO | 2016/030897 A1 | 3/2016 |
| WO | 2016/203320 A2 | 12/2016 |
| WO | 2017/046799 A1 | 3/2017 |
| WO | 2017/168411 A1 | 10/2017 |
| WO | 2017/195205 A1 | 11/2017 |
| WO | 2017/195208 A1 | 11/2017 |
| WO | 2018/009920 A1 | 1/2018 |
| WO | 2018009920 A1 | 1/2018 |
| WO | 2018/102748 A1 | 6/2018 |
| WO | 2019/035084 A1 | 2/2019 |
| WO | 2019/097387 A1 | 5/2019 |
| WO | 2019/102277 A1 | 5/2019 |
| WO | 2019/198094 A1 | 10/2019 |
| WO | 2021/079305 A1 | 4/2021 |
| WO | 2021/079306 A1 | 4/2021 |

OTHER PUBLICATIONS

F. Boray Tek et al. "Parasite detection and identification for automated thin blood film malaria diagnosis"; Computer Vision and Image Understanding vol. 114, Issue 1, Jan. 2010, pp. 21-32.

A European Examination Report dated Dec. 9, 2019 which issued during the prosecution of Applicant's European App No. 16782094.3.

Notice of Allowance dated Mar. 2, 2020, which issued during the prosecution of U.S. Appl. No. 16/657,473.

A European Examination Report dated Feb. 1, 2019 which issued during the prosecution of Applicant's European App No. 17717000.8.

A European Examination Report dated Sep. 3, 2019 which issued during the prosecution of Applicant's European App No. 17717000.8.

A European Examination Report dated Apr. 8, 2020 which issued during the prosecution of Applicant's European App No. 17717000.8.

A European Examination Report dated Apr. 6, 2020 which issued during the prosecution of Applicant's European App No. 17726036.1.

A European Examination Report dated Feb. 11, 2020 which issued during the prosecution of Applicant's European App No. 17728277.9.

Biérler, S., et al., "Improved detection of *Trypanosoma brucei* by lysis of red blood cells, concentration and LED fluorescence microscopy", Acta Tropica, vol. 121, Issue 2, 2012, pp. 135-140 (6 pages total).

Chiodini, P. L., et al., "Rapid diagnosis of malaria by fluorescence microscopy", The Lancet, vol. 337, pp. 624-625, Mar. 9, 1991 (2 pages total).

Communication dated Apr. 2, 2015, which issued during the prosecution of U.S. Appl. No. 13/338,291.

Communication dated Feb. 22, 2018, which issued during the prosecution of U.S. Appl. No. 14/369,251.

Communication dated Dec. 24, 2018 from the Intellectual Property India Patent Office in application No. 3592/MUMNP/2015.

Communication dated Jan. 28, 2019 from the United States Patent and Trademark Office in U.S. Appl. No. 15/174,490.

Communication dated Jan. 31, 2019 from the Intellectual Property India Patent Office in application No. 5069/DELNP/2012.

Communication dated Mar. 23, 2018 from the Intellectual Property India Patent Office in application 4263/DELNP/2014.

Communication dated Nov. 16, 2018 from the United States Patent and Trademark Office in U.S. Appl. No. 14/914,329.

Communication dated Sep. 25, 2015 from the United States Patent and Trademark Office in U.S. Appl. No. 13/338,291.

Communication dated Oct. 29, 2014 from the United States Patent and Trademark Office in U.S. Appl. No. 13/338,291.

Diagnostic Procedures, "Blood Specimens: Microscopic Examination", 2009, http://mcdinternational.org/trainings/malaria/english/dpdx5/HTML/Frames/DiagnosticProcedures/body_dp_bloodexamin (2 pages total).

Gallo, V., et al., "Simultaneous determination of phagocytosis of *Plasmodium falciparum*-parasitized and non-parasitized red blood cells by flow cytometry", Malaria Journal, vol. 11, No. 428, 2012, pp. 1-11 (11 pages total).

International Search Report and Written Opinion, dated Aug. 8, 2017 from the International Bureau in counterpart International application No. PCT/IL2017/050523.

(56) References Cited

OTHER PUBLICATIONS

International Search Report and Written Opinion, dated May 18, 2017 from the International Bureau in counterpart International application No. PCT/IL2017/050363.
International Search Report and Written Opinion, dated Aug. 30, 2017 from the International Bureau in counterpart International application No. PCT/IL2017/050526.
International Search Report and Written Opinion, dated Jul. 27, 2012 from the International Bureau in counterpart International application No. PCT/IL2011/000973.
Jager, M.M., et al., "Five-minute Giemsa stain for rapid detection of malaria parasites in blood smears", Tropical Doctor, vol. 41, Jan. 2011, pp. 33-35 (3 pages total).
Joanny, F., et. al., "In Vitro Activity of Fluorescent Dyes against Asexual Blood Stages of Plasmodium falciparum", Antimicrobial Agents and Chemotherapy, vol. 56, No. 11, Nov. 2012, pp. 5982-5985 (4 pages total).
Kumar, A., et al., "Enhanced Identification of Malarial Infected Objects using Otsu Algorithm from Thin Smear Digital Images", International Journal of Latest Research in Science and Technology, vol. 1, Issue 2, 2012, pp. 159-163 (5 pages total).
Le, M.-T., et al., "A novel semi-automatic image processing approach to determine Plasmodium falciparum parasitemia in Giemsa-stained thin blood smears", BioMed Central Cell Biology, Mar. 28, 2008, vol. 9, No. 15, pp. 1-12 (12 pages total).
Garcia, et al., "M15-A Laboratory Diagnosis of Blood-borne Parasitic Diseases; Approved Guideline", Clinical and Laboratory Standards Institute, vol. 20, No. 12, Jun. 2000 (13 pages total).
Mendiratta, DK, et al., "Evaluation of Different Methods for Diagnosis of P. Falciparum Malaria", Indian Journal of Medical Microbiology, 2006, vol. 24, No. 1, pp. 49-51 (3 pages total).
Moon, S., et al., "An Image Analysis Algorithm for Malaria Parasite Stage Classification and Viability Quantification", PLOS One, vol. 8, Issue 4, Apr. 2013, pp. 1-12 (12 pages total).
Notice of Allowance dated Jan. 19, 2016, from the United States Patent and Trademark Office in application No. 13/338,291.
Notice of Allowance dated Mar. 10, 2016 from the United States Patent and Trademark Office in U.S. Appl. No. 13/338,291.
Pasini, E., et al., "A novel live-dead staining methodology to study malaria parasite viability", Malaria Journal, vol. 12, No. 190, 2013, pp. 1-10 (10 pages total).
Piruska, A., et al., "The autofluorescence of plastic materials and chips measured under laser irradiation", Lab on a Chip, vol. 5, 2005, pp. 1348-1354 (7 pages total).
Sheikh, H., et al., "Blood Cell Identification Using Neural Networks", Proceedings of the IEEE 2nd Annual Northeast Bioengineering Conference, Mar. 1996, pp. 119-120 (2 pages total).
Tek, F. et al., "Parasite detection and identification for automated thin blood film malaria diagnosis", Computer Vision and Image Understanding, vol. 114, Issue 1, 2010, pp. 21-32 (12 pages total).
Unitaid, "Malaria Diagnostics Technology and Market Landscape", 2nd Edition, Jul. 2014, pp. 1-140 (148 pages total).
Wissing, et al., "Illumination of the Malaria Parasite Plasmodium falciparum Alters Intracellular pH", The Journal of Biological Chemistry, vol. 277, No. 40, Issue of Oct. 4, pp. 37747-37755, 2002, (10 pages total).
Wright, J., "A Rapid Method For The Differential Staining of Blood Films And Malarial Parasites", Journal of Medical Research, vol. 7, No. 1, 1902, pp. 138-144 (7 pages total).
Yao, LN., et al., "Pathogen Identification and Clinical Diagnosis for One Case Infected with Babesia", Chinese Journal of Parasitology Parasitic Diseases, vol. 30, No. 2, Apr. 2012, pp. 118-121 (4 pages total).
Communication dated Nov. 18, 2014 from the Canadian Patent Office in application No. 2,655,024.
Communication dated Feb. 22, 2018, issued by the United States Patent and Trademark Office in the prosecution of U.S. Appl. No. 14/369,251.
Communication dated Mar. 23, 2018, issued by the Intellectual Property Office of India in co-pending Indian Application No. 4263/DELNP/2014.
An Office Action dated Jan. 10, 2018, which issued during the prosecution of U.S. Appl. No. 15/083,610.
Matcher, S. J., M. Cope, and D. T. Delpy. "Use of the water absorption spectrum to quantify tissue chromophore concentration changes in near-infrared spectroscopy." Physics in medicine and biology 38.1 (1994): 177-196.
Rappaz, Benjamin, et al. "Comparative study of human erythrocytes by digital holographic microscopy, confocal microscopy, and impedance volume analyzer." Cytometry Part A 73.10 (2008): 895-903.
Ross, Nicholas E., et al. "Automated image processing method for the diagnosis and classification of malaria on thin blood smears." Medical and Biological Engineering and Computing 44.5 (2006): 427-436.
Houri-Yafin, A., et al. "An enhanced computer vision platform for clinical diagnosis of malaria." Malar Control Elimin 5.138.10 (2016): 4172.
Ahirwar, Neetu, Sapnojit Pattnaik, and Bibhudendra Acharya. "Advanced image analysis based system for automatic detection and classification of malarial parasite in blood images." International Journal of Information Technology and Knowledge Management 5.1 (2012): 59-64.
An Office Action dated Aug. 4, 2017, which issued during the prosecution of U.S. Appl. No. 14/369,251.
An Office Action dated Jun. 13, 2017, which issued during the prosecution of U.S. Appl. No. 14/285,672.
An Office Action dated Jul. 11, 2017, which issued during the prosecution of U.S. Appl. No. 15/174,490.
Osibote, O. A., et al. "Automated focusing in bright-field microscopy for tuberculosis detection." Journal of microscopy 240.2 (2010): 155-163.
Shen, Feimo, Louis Hodgson, and Klaus Hahn. "Digital autofocus methods for automated microscopy." Methods in enzymology 414 (2006): 620-632.
Wu, Qiang, Fatima Merchant, and Kenneth Castleman. Microscope image processing. Chapter 16, "Autofocusing", pp. 441-467, Academic press, 2010.
Purwar, Yashasvi, et al. "Automated and unsupervised detection of malarial parasites in microscopic images." Malaria journal 10.1 (2011): 364.
Frean, John. "Microscopic determination of malaria parasite load: role of image analysis." Microscopy: Science, technology. Applications, and Education (2010): 862-866.
Price, Jeffrey H., and David A. Gough. "Comparison of phase—contrast and fluorescence digital autofocus for scanning microscopy." Cytometry 16.4 (1994): 283-297.
Vink, J. P., etal. "An automatic vision based malaria diagnosis system" Journal of microscopy 250.3(2013): 166-178.b.
Chong, Shau Poh, Shilpa Pant, and Nanguang Chen. "Line-scan focal modulation microscopy for rapid imaging of thick biological specimens." S PIE/OS A/IEEE Asia Communications and Photonics. International Society for Optics and Photonics, 2011.
Yang, Ming, and Li Luo. "A rapid auto-focus method in automatic microscope." Signal Processing, 2008, ICSP 2008. 9th International Conference on. IEEE, 2008.
Anand, A., et al. "Automatic identification of malaria-infected RBC with digital holographic microscopy using correlation algorithms." Photonics Journal, IEEE 4.5 (2012): 1456-1464.
Ortyn, William E., et al. "Extended depth of field imaging for high speed cell analysis." Cytometry Part A 71.4 (2007): 215-231.
Sun, Yu, Stefan Duthaler, and Bradley J. Nelson. "Autofocusing algorithm selection in computer microscopy." Intelligent Robots and Systems, 2005,(IROS 2005). 2005 IEEE/RSJ International Conference on. IEEE, 2005.
Keiser, J., et al. "Acridine Orange for malaria diagnosis: its diagnostic performance, its promotion and implementation in Tanzania, and the implications for malaria control." Annals of tropical medicine and parasitology, 96.7 (2002): 643-654.
Shute, G. T., and T. M. Sodeman. "Identification of malaria parasites by fluorescence microscopy and acridine orange staining." Bulletin of the World Health Organization, 48.5 (1973): 591.

(56) References Cited

OTHER PUBLICATIONS

Kawamoto, Fumihiko, "Rapid diagnosis of malaria by fluorescence microscopy with light microscope and interference filter". The Lancet, vol. 337, pp. 200-202, Jan. 26, 1991.
Emma Eriksson et al: "Automated focusing of nuclei for time lapse experiments on single cells using holographic optical tweezers", Optics Express, vol. 17, No. 7, Mar. 24, 2009, pp. 5585-5594.
Kawamoto, F. and P. F. Billingsley. "Rapid diagnosis of malaria by fluorescence microscopy." Parasitology today 8.2 (1992): 69-71.
An International Search Report and a Written Opinion both dated Jan. 15, 2016, which issued during the prosecution of Applicant's PCT/IL2015/050864.
Tek, F. Boray, Andrew G. Dempster, and Izzet Kale. "Computer vision for microscopy diagnosis of malaria." Malaria Journal 8.1 (2009): 153.
Merchant, et al. "The essential guide to image processing", chapter 27, "Computer assisted Microscopy", pp. 777-831. Academic Press, 2009.
Thung, Ferdian, and Iping Supriana Suwardi. "Blood parasite identification using feature based recognition." Electrical Engineering and Informatics (ICEEI), 2011 International Conference on. IEEE, 2011.
Bacus, J.W., 1985. Cytometric approaches to red blood cells. Pure and Applied Chemistry, 57(4), pp. 593-598.
Centers for Disease Control and Prevention. "DPDx—Laboratory Identification of Parasitic Diseases of Public Health Concern", <http://www.cdc.gov/dpdx/diagnosticProcedures/blood/microexam.html>, Nov. 29, 2013.
An International Search Report and a Written Opinion both dated Feb. 12, 2015, which issued during the prosecution of Applicant's PCT/IL2014/050770.
U.S. Appl. No. 61/870,106, filed Aug. 26, 2013.
The use of fluorescence enhancement to improve the microscopic diagnosis of falciparum malaria Malaria Journal 2007, 6:89 http://www.malariajonmal.eom/content/6/1/89, Rebecca Guy, Paul Liu, Peter Pennefather and Ian Crandall (Jul. 6, 2007).
Leif, "Methods for Preparing Sorted Cells as Monolayer Specimens", Springer Lab Manuals, Section 7—Chapter 5, pp. 592-619, (2000).
An Office Action dated Oct. 5, 2016, which issued during the prosecution of U.S. Appl. No. 14/285,672.
Groen F C A et al: "A Comparison of Different Focus Functions for Use in Autofocus Algorithms", Cytometry, Alan Liss, New York, US, vol. 6, No. 2, Mar. 1, 1985 (Mar. 1, 1985), pp. 81-91.
Andrew Gordon et al: "Supplementary Note to Gordon et al: "Single-cell quantification of molecules . . . "". Nature Methods, Jan. 21, 2007, pp. 1-35.
Andrew Gordon et al: "Single-cell quantification of molecules and rates using open-source microscope-based cytometry", HHS Public Access Author Manuscript, vol. 4, No. 2, Jan. 21, 2007, pp. 175-181.
European Search Report dated Dec. 14, 2016. which issued during the prosecution of Applicant's European App No. 14800352.8.
An International Search Report and a Written Opinion both dated Sep. 29, 2014. which issued during the prosecution of Applicant's PCT/IL2014/050423.
An International Search Report and a Written Opinion both dated Apr. 18. 2013, which issued during the prosecution of Applicant's PCT/IL2012/050556.
An International Search Report and a Written Opinion both dated Oct. 30, 2014, which issued during the prosecution of Applicant's PCT/IL2014/050585.
Notice of Allowance dated Jan. 11, 2016, which issued during the prosecution of U.S. Appl. No. 14/440,864.
High-content live cell imaging with RNA probes: advancements in high-throughput antimalarial drug discovery BMC Cell Biology 2009, 10:45 www.biomedcentral.com/1471-2121/10/45 Serena Cervantes, Jacques Prudhomme, David Carter, Krishna G Gopi, Qian Li, Young-Tae Chang and Karine G Le Roch (Jun. 10, 2009).
Plasmodium yoelii: A differential fluorescent technique using Acridine Orange to identify infected erythrocytes and reticulocytes in Duffy knockout mouse. Experimental Parasitology vol. 110, Issue 1, May 2005, pp. 80-87. <http://www.sciencedirect.com/science/article/_pii/S001448940500038X>: Lili Xu, Asok Chaudhuri (May 31, 2005).
Notice of Allowance dated Dec. 30, 2015, which issued during the prosecution of U.S. Appl. No. 14/440,864.
Zahniser et al., Automated Slide Preparation System for the Clinical Laboratory, Cytometry, vol. 26, No. 10, pp. 30-64, (1996).
Moody, "Rapid Diagnostic Tests for Malaria Parasites", Clinical Microbiology Reviews, vol. 15, No. 1, pp. 66-78, (2002).
Knesel, "Roche Image Analysis Systems, Inc.", Acta Cytologica, vol. 40, pp. 60-66, (1996).
Life Technologies Corporation, "Counting blood cells with Countess Automated Cell Counter" pdf, four pages, (2009).
An Office Action dated Mar. 2, 2017. which issued during the prosecution of U.S. Appl. No. 14/369,251.
An International Search Report and a Written Opinion both dated Jan. 23, 2017, which issued during the prosecution of Applicant's PCT/IL2016/051025.
European Search Report dated Mar. 23, 2017. which issued during the prosecution of Applicant's European App No. 14839661.7.
An International Preliminary Report on Patentability dated Feb. 28, 2017, which issued during the prosecution of Applicant's PCT/IL2015/050864.
Roma, P. M. S., et al. "Total three-dimensional imaging of phase objects using defocusing microscopy: Application to red blood cells." Applied Physics Letters 104.25 (2014): 251107.
Agero, U., Mesquita, L.G., Neves, B.R.A., Gazzinelli, R.T. and Mesquita, O.N., 2004. Defocusing microscopy. Microscopy research and technique, 65(3), pp. 159-165.
Yazdanfar, S., Kenny, K.B., Tasimi, K., Corwin, A.D., Dixon, E.L. and Filkins, R.J., 2008. Simple and robust image-based autofocusing for digital microscopy. Optics express, 16(12), pp. 8670-8677.
Bravo-Zanoguera, M.E., Laris, C.A., Nguyen, L.K., Oliva, M. and Price, J.H., 2007. Dynamic autofocus for continuous-scanning time-delay-and-integration image acquisition in automated microscopy. Journal of biomedical optics, 12(3), pp. 034011-034011.
U.S. Appl. No. 62/042,388, filed Aug. 27, 2014.
Office Action dated Jun. 15, 2018 from the United States Patent and Trademark Office in copending U.S. Appl. No. 14/369,251.
Office Action dated Jun. 29, 2018 from the United States Patent and Trademark Office in copending U.S. Appl. No. 15/174,490.
An Extended European Search Report issued for European Patent Application No. 21164814.2 dated Jun. 9, 2021.
Third Office Action dated Jul. 12, 2021 which issued during the prosecution of Chinese Patent Application No. 201680053431.1.
Non-Final Office Action dated Jul. 27, 2021, which issued during the prosecution of U.S. Appl. No. 16/851,686.
Non-Final Office Action dated Aug. 19, 2021, which issued during the prosecution of U.S. Appl. No. 16/098,893.
First Office Action dated Aug. 4, 2021 which issued during the prosecution of Chinese Patent Application No. 201780027908.3.
An Examination Report dated Mar. 4, 2021 which issued during the prosecution of Indian Patent Application No. 201817036130.
An Examination Report dated May 5, 2021 which issued during the prosecution of Indian Patent Application No. 201817012117.
Notice of Allowance dated Aug. 3, 2021, which issued during the prosecution of U.S. Appl. No. 16/851,410.
An International Search Report and Written Opinion for Application No. PCT/IB2020/061731 dated Feb. 10, 2021.
Invitation to pay fees and Partial Search Report issued for PCT Application No. PCT/IB2020/061732 dated Mar. 10, 2021.
Invitation to pay fees and Partial Search Report issued for PCT Application No. PCT/IB2020/061736 dated Mar. 12, 2021.
Invitation to pay fees and Partial Search Report issued for PCT Application No. PCT/IB2020/061728 dated Mar. 15, 2021.
International Search Report issued for PCT Application No. PCT/IB2020/061724 dated Mar. 10, 2021.
An International Search Report and Written Opinion for PCT Application No. PCT/IB2020/061732 dated May 7, 2021.

(56) References Cited

OTHER PUBLICATIONS

International Search Report and Written Opinion for PCT Application No. PCT/IB2020/061728 dated May 7, 2021.
International Search Report and Written Opinion for PCT Application No. PCT/IB2020/061736 dated May 3, 2021.
Non-Final Office Action dated Jun. 17, 2021 which issued during the prosecution of U.S. Appl. No. 16/851,410.
Notice of Allowance dated May 19, 2021 which issued during the prosecution of U.S. Appl. No. 16/099,270.
A Restriction Requirement issued by the USPTO dated Oct. 19, 2020 for U.S. Appl. No. 16/099,270.
Non-Final Office Action dated Oct. 6, 2021, which issued during the prosecution of U.S. Appl. No. 17/063,320.
Saraswat, et al. "Automated microscopic image analysis for leukocytes identification: A survey", ABV-Indian Institute of Information Technology and Management, Gwalior, India, Micron, 2014, vol. 65, pp. 20-33.
Hiremath, P. S,. et al., "Automated Identification and Classification of White Blood Cells (Leukocytes) in Digital Microscopic Images", IJCA Special Issue on "Recent Trends in Image Processing and Pattern Recognition" RTIPPR, 2010, pp. 59-63.
Witt, et al. "Establishing traceability of photometric absorbance values for accurate measurements of the haemoglobin concentration in blood.", Metrologia 50 (2013) 539-548.
Putzu, et al., "Leucocyte classification for leukaemia detection using image processing techniques.", Artificial Intelligence in Medicine, vol. 63, No. 3, Nov. 1, 2014, pp. 1-31.
Varga, et al., "An automated scoring procedure for the micronucleus test by image analysis", Mutagenesis vol. 19 No. 5 pp. 391-397, 2004.
Ran, Qiong et al. "Spatial-spectral blood cell classification with microscopic hyperspectral imagery", Proc. SPIE 10461, AOPC 2017: Optical Spectroscopy and Imaging, 1046102 (Oct. 24, 2017) (12 pages total).
Omucheni et al. "Application of principal component analysis to multispectral-multimodal optical image analysis for malaria diagnostics", Malaria Journal 2014, 13:485 http://www.malariajournal.com/content/13/1/485 (11 pages total).
Ben-Suliman—2018—"Computerized Counting-Based System for Acute Lymphoblastic Leukemia Detection in Microscopic Blood Images" 27th International Conference on Artificial Neural Networks, Rhodes, Greece, Oct. 4-7, 2018, Proceedings, Part II, pp. 167-178.
An Office Action dated Dec. 8, 2020 for Japanese Patent Application No. 2018/512961.
An Examination Report dated Dec. 7, 2020 for Australian Patent Application No. 2016322966.
An Office Action dated Jan. 11, 2021 for U.S. Appl. No. 16/098,893.
An Examination Report dated Apr. 29, 2021 for Australian Patent Application No. 2016322966.
International Search Report issued for PCT Application No. PCT/IB2020/059924 dated Mar. 22, 2021.
International Search Report issued for PCT Application No. PCT/IB2020/059925 dated Mar. 26, 2021.
Invitation to pay fees and Partial Search Report issued for PCT Application No. PCT/IB2020/059924 dated Jan. 28, 2021.
Invitation to pay fees and Partial Search Report issued for PCT Application No. PCT/IB2020/059925 dated Feb. 4, 2021.
Communication dated Mar. 30, 2021 from the Japanese Patent Office in Application No. 2018-558180.
Communication dated Jan. 29, 2021 from the US Patent and Trademark Office in U.S. Appl. No. 16/099,270.
An Office Action dated Aug. 24, 2020 for U.S. Appl. No. 16/098,893.
A Chinese Office Action and dated May 22, 2020. which issued during the prosecution of Chinese Application No. 201680053431.1.
Steven S.S. Poon, et al., "Automated Image Detection and Segmentation in Blood Smears", Cytometry, 1992, pp. 766-774, vol. 13 (9 pages total).

John F. Brenner, et al.,"An Automated Microscope for Cytologic Research a Preliminary Evaluation", The Journal of Histochemistry and Cytochemistry, 1976, pp. 100-111, vol. 24, No. 1 (12 pages total).
S A H Jahanmehr, et al.,"Simple Technique for Fluorescence Staining of Blood Cells with Acridine Orange", Journal of Clinical Pathology, Feb. 12, 1987, pp. 926-929 (4 pages total).
Anne Fohlen-Walter, PhD, et al., "Laboratory Identification of Cryoglobulinemia From Automated Blood Cell Counts, Fresh Blood Samples, and Blood Films", American Society for Clinical Pathology, Am J Clin Pathol, 2002, pp. 606-614, vol. 117 (9 pages total).
Caicai Wu, et al., "Feasibility study of the spectroscopic measurement of oxyhemoglobin using whole blood without pre-treatment", The Analyst, Mar. 1998, pp. 477-481, vol. 123 (5 pages total).
C. Briggs, et al., "Continuing developments with the automated platelet count", Blackwell Publishing Ltd, International Journal of Laboratory Hematology, Jan. 18, 2007, pp. 77-91, vol. 29 (15 pages total).
International Search Report in International Application No. PCT/IB2018/058861, dated Apr. 8, 2019.
Written Opinion in International Application No. PCT/IB2018/058861, dated Apr. 8, 2019.
Office Action dated Apr. 4, 2019, which issued during the prosecution of U.S. Appl. No. 14/914,329.
Notice of Allowance dated Mar. 20, 2019, which issued during the prosecution of U.S. Appl. No. 15/506,997.
Office Action dated Jun. 5, 2019, which issued during the prosecution of U.S. Appl. No. 15/174,490.
Office Action dated Jun. 4, 2019, which issued during the prosecution of U.S. Appl. No. 14/369,251.
A European Examination Report issued for European Patent Application No. 17728277.9 dated Dec. 23, 2021.
A Non-Final Office Action dated May 26, 2022 which issued during the prosecution of U.S. Appl. No. 17/083,775.
An Office Action dated May 31, 2022 which issued during the prosecution of U.S. Appl. No. 17/083,659.
An Office Action dated May 6, 2022 which issued during the prosecution of U.S. Appl. No. 16/763,810.
Examination Report issued by the Indian Patent Office dated Jun. 28, 2022 in Indian Patent Application No. 202047019700.
Notice of Allowance dated Nov. 10, 2021, which issued during the prosecution of U.S. Appl. No. 16/851,686.
Notice of Allowance dated Jan. 21, 2022, which issued during the prosecution of U.S. Appl. No. 16/098,893.
Notice of Allowance dated Nov. 5, 2021, which issued during the prosecution of U.S. Appl. No. 16/851,410.
Supplemental Notice of Allowance dated Nov. 12, 2021, which issued during the prosecution of U.S. Appl. No. 16/851,686.
An Office Action dated Mar. 3, 2022, which issued during the prosecution of U.S. Appl. No. 17/063,320.
An Office Action dated Aug. 2, 2022, which issued during the prosecution of Japanese Patent Application No. 2021-145455.
An Examination Report dated Aug. 25, 2022, which issued during the prosecution of Australian Patent Application No. 2017263807.
An Office Action dated Aug. 30, 2022 which issued during the prosecution of Japanese Patent Application No. 2020-526176.
An Office Action dated Sep. 13, 2022 which issued during the prosecution of Japanese Patent Application No. 2021-157849.
Hideto Miura, "How to regard as how to consider the poikilocyte in urine an erroneous decision factor", Modern Medical Laboratory, Sep. 1, 2002, vol. 30, No. 9, pp. 862-864 (6 pages total).
Jun Hashimoto, "Morphological Studies of Urinary Red Blood Cells in Renal and Urinary Tract Disorders (II) Use of Wright's Stain in Differential Diagnosis between Renal and Urinary Tract Disorders" Kawasaki Medical Congress Magazine, Mar. 1989, vol. 15, No. 1, pp. 94-101 (9 pages total).
D F Birch et al., "The research on the differential diagnosis of the kidney urinary tract obstacle by glomerular or non-glomerular", Lancet, Oct. 20, 1979, vol. 2, No. 8147, pp. 845-846 (3 pages total).
A First Examination Report dated Sep. 19, 2022, which issued during the prosecution of Indian Patent Application No. 201817040226.
An Office Action dated Oct. 3, 2022 which issued during the prosecution of U.S. Appl. No. 16/763,810.

(56) References Cited

OTHER PUBLICATIONS

An Office Action dated Oct. 25, 2022 which issued during the prosecution of Canadian Application No. 2,998,829 (SDX044).
An Office Action dated Oct. 5, 2022 which issued during the prosecution of Brazilian Application No. 112018005099-7.
An Office Action dated Nov. 25, 2022 which issued during the prosecution of Brazilian Application No. 122020017765-9.
An Office Action dated Dec. 9, 2022 which issued during the prosecution of U.S. Appl. No. 17/083,647.
An Office Action dated Dec. 28, 2022 which issued during the prosecution of Russian Patent Application No. 2022112399.
An Office Action dated Dec. 28, 2022 which issued during the prosecution of Russian Patent Application No. 2022112393.
An Office Action dated Jan. 6, 2023 which issued during the prosecution of U.S. Appl. No. 17/063,320.
An Office Action dated Sep. 2, 2022 which issued during the prosecution of U.S. Appl. No. 17/063,320.
An Office Action dated Jan. 5, 2023 which issued during the prosecution of Chinese Patent Application No. 201880079888.9.
An Examination Report dated Jan. 23, 2023, which issued during the prosecution of Australian Patent Application No. 2022200112.
An Office Action dated Jan. 19, 2023 which issued during the prosecution of U.S. Appl. No. 17/490,767.
An Office Action dated Nov. 25, 2022 which issued during the prosecution of U.S. Appl. No. 17/082,483.
Office Action dated Mar. 2, 2023 in Canadian Application No. 3,018,536.

\* cited by examiner

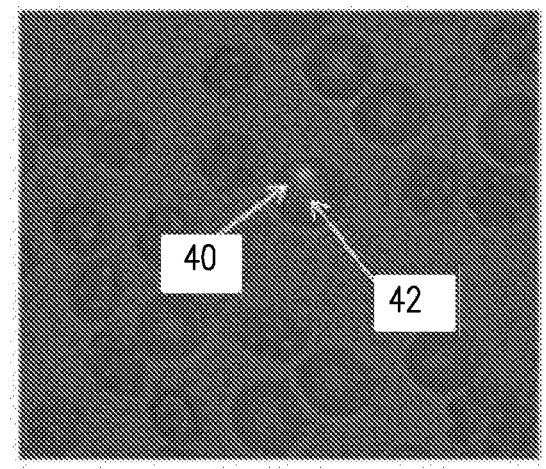
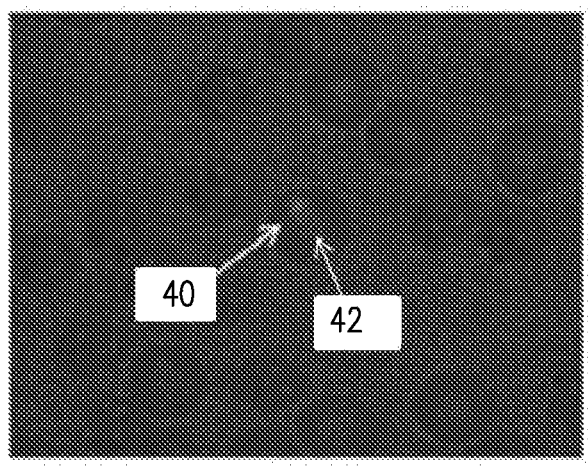
FIG. 2A             FIG. 2B
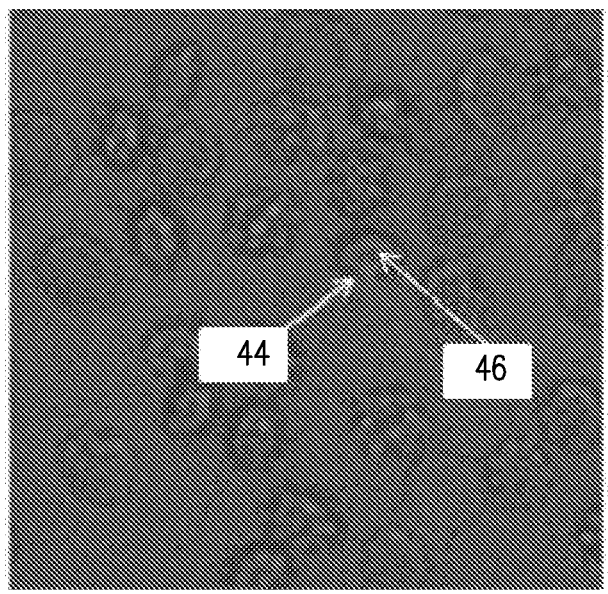
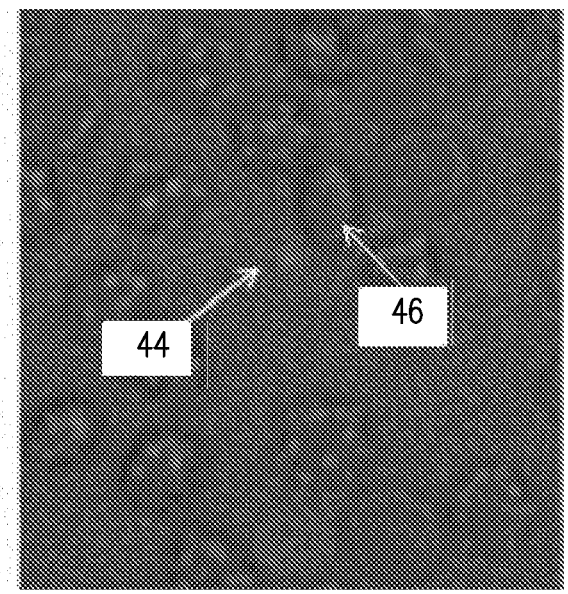
FIG. 3A             FIG. 3B

DISTINGUISHING BETWEEN BLOOD SAMPLE COMPONENTS

CROSS-REFERENCE TO RELATED APPLICATIONS

The present application claims priority from U.S. Provisional Patent Application No. 62/315,223 to Eshel, filed Mar. 30, 2016, entitled "Distinguishing between blood sample components."

The above-referenced application is incorporated herein by reference.

FIELD OF EMBODIMENTS OF THE INVENTION

The present invention relates to methods and systems for analyzing bodily fluids, and particularly to methods and systems for analyzing blood samples.

BACKGROUND

*Plasmodium* is a genus of eukaryotic parasites (protozoa) known to cause malaria. The life cycle of *Plasmodium* includes a stage during which *Plasmodium* parasites principally inhabit erythrocytes.

A primary method of detection of such infections is the microscopic examination of blood samples, and visual confirmation of the presence and concentration of the parasite. Staining the blood sample with a stain or dye prior to microscopic examination is often used to visually highlight the parasites. Microscopic examination of blood samples may include preparing a monolayer of the cells in the sample, thereby allowing examination of the majority of cells in any given field of vision.

Babesiosis is an emerging disease caused by the pathogen *Babesia*. Similarly to *Plasmodium*, *Babesia*'s life cycle also includes an intra-erythrocytic stage. Babesiosis is endemic to the US, particularly New England. The transmitting vector is a tick (that also transmits Lyme disease). Though Babesiosis infection is mostly asymptomatic in healthy adults, if it is transmitted through transfusion of an infected blood unit, it may be fatal in immunocompromised, splenectomized or elderly recipients.

SUMMARY OF EMBODIMENTS

In accordance with some applications of the present invention, first and second images of a blood sample are acquired at respective times. A computer processor determines whether, between acquisitions of the first and second images, there was relative motion between at least one erythrocyte within the sample and at least one entity within the sample, by comparing the first and second images to one another. At least partially in response thereto, the computer processor determines whether the entity is an extra-erythrocytic or an intra-erythrocytic entity.

For example, based upon its dimensions and or other characteristics, the entity may be a platelet candidate (i.e., an entity that could potentially be a platelet), and/or an intra-erythrocytic-parasite candidate (i.e., an entity that could potentially be an intra-erythrocytic parasite, such as *Plasmodium* and/or *Babesia*). At times, the entity is an entity the dimensions or other characteristics of which (e.g., the location of which with respect to an erythrocyte), are such that the entity appears to be either a platelet or an intra-erythrocytic parasite, and it is unclear which of the two it is. In response to determining that (a) in the first image the entity is disposed in the vicinity of an erythrocyte, and that (b) there was relative motion between the erythrocyte and the entity between acquisitions of the first and second images, the computer processor may confirm that the entity is a platelet.

Alternatively, in response to determining that (a) in the first image the entity is disposed in the vicinity of an erythrocyte, and that (b) there was little or no relative motion between the erythrocyte and the entity between acquisitions of the first and second images, the computer processor may determine that the entity is an intra-erythrocytic entity. Based at least in part upon determining that the entity is an intra-erythrocytic entity, the computer processor may determine that the entity is an intra-erythrocytic parasite, such as *Plasmodium* and/or *Babesia*.

Alternatively or additionally, the determination of whether the entity is an intra-erythrocytic entity or an extra-erythrocytic entity, is used as data in blood sample analysis. For example, the computer processor may perform a complete blood count or part of a blood count, which includes a count of platelets, using, as data, the determination of whether the entity is an extra-erythrocytic entity (and therefore a platelet) or an intra-erythrocytic entity.

In general, in the context of the specification and the claims of the present application, an entity being disposed in the vicinity of an erythrocyte should be interpreted as including an entity that appears to be completely or overlapping with an erythrocyte, partially overlapping with an erythrocyte, abutting an erythrocyte, or an entity disposed within a given physical distance, or within a given number of pixels of an erythrocyte.

For some applications, the computer processor does not necessarily determine whether or not the entity is an intra-erythrocytic entity or an extra-erythrocytic entity, but rather determines a likelihood of the entity being one or the other of these, and performs analysis of the blood sample based upon the determined likelihood.

*Plasmodium* parasites and *Babesia* parasites found within erythrocytes sometimes have similar dimensions to platelets and may be stained by the same staining substances (e.g. staining substances that stain nucleic acids). Therefore, platelets located in the vicinity of an erythrocyte may be confused with *Plasmodium* parasites and/or *Babesia* parasites, leading to false positive detection of *Plasmodium* and/or *Babesia*. In addition, in blood sample analysis (for example, in a complete or partial blood count), it may be useful to distinguish between platelets and intra-erythrocytic entities. For example, such a distinction may be used in order to increase the accuracy of a platelet count, in order to reduce the likelihood of confusing between platelets and intra-erythrocytic entities, such as parasitic entities, Howell Jolly bodies, reticular networks of ribosomal DNA within reticulocytes, Heinz bodies, Pappenheimer bodies, and/or nuclei within nucleated erythrocytes, etc., and/or in order to increase the accuracy of a count of such intra-erythrocytic entities. It is noted that some of the aforementioned intra-erythrocytic entities are typically found in immature erythrocytes (e.g., inside reticulocytes or nucleated erythrocytes).

It is noted that, under some circumstances, platelets that are disposed in the vicinity of erythrocytes may be differentiated from parasites (or other intra-erythrocytic bodies) based on properties such as staining intensity, which may be significantly higher for parasites, for example, than for platelets. In such cases, the number of platelets that might be falsely identified as being inside an erythrocyte may be very small. However, in some cases blood samples include a substantial amount of platelets that have the appearance of an intra-erythrocytic entity. In some cases, there are 5-30 of such platelets per 500,000 erythrocytes. For some applications, the apparatus and methods described herein are used to distinguish between such platelets and intra-erythrocytic entities, such as parasites (e.g., *Plasmodium*, and/or *Babesia*).

Typically, images are acquired while the blood sample is in a preparation within which erythrocytes and other entities within the sample are not maintained in fixed positions.

For example, the blood sample may be prepared within a monolayer, as described, for example, in PCT Application Publication WO 15/001553 to Pollack, which is incorporated herein by reference. The aforementioned reference describes introducing a cell suspension comprising red blood cells onto a base surface of a carrier having a vertical height that is greater than or equal to a vertical depth of the cell suspension when on the base carrier. The cells in the cell suspension are allowed to settle (without applying any force thereon) on the base surface of the carrier to form a monolayer of cells on the base surface of the carrier, without fixing the cells in position. Optionally, the solution has a vertical height of between 20 micrometers and 1,000 micrometers. Preparing the sample in this manner allows motion of bodies within the sample with respect to one another, even after the cells have settled and analysis thereof has begun. For some applications, between acquisitions of the first and second images, the sample is moved, vibrated, and/or agitated, thereby causing increased movement of bodies within the sample with respect to one another.

For some applications, rather than automatically comparing the first image to the second image, a first set of one or more images of the blood sample is acquired. A computer processor analyzes the first set of one or more images of the blood sample, in order to determine whether there are any entities within the images for which it would be desirable to determine whether the entity is an extra-erythrocytic entity or an intra-erythrocytic entity. In response to the analysis, the computer processor may automatically acquire a second set of one or more images of the blood sample, and/or may generate an output indicative of a recommendation to acquire a second set one or more images of the blood sample. For example, the computer processor may acquire the second set of images, and/or generate the output, in response to determining that there are one or more entities that overlap with an erythrocyte and that may be either a platelet or an intra-erythrocytic entity (e.g., an intra-erythrocytic parasite, such as *Plasmodium*, and/or *Babesia*).

For some applications, in response to the analysis of the first set of images, the computer processor selects to compare the first set of one or more images of the blood sample to a second set of one or more images of the blood sample that were acquired after acquisition of the first set of one or more images of the blood sample. For some such applications, the second set of one or more images is acquired, regardless of the results of the analysis of the first set of one or more images, but the first set of images is compared to the second set of images, only if the analysis of the first set of images indicates that there is a reason for doing so. For some applications, the second set of one or more images of the blood sample is only acquired, based upon the computer processor selecting to compare the first set of one or more images of the blood sample to a second set of one or more images of the blood sample. For example, as described hereinabove, the second set of one or more images of the blood sample may be acquired automatically, or an output may be generated by the computer processor that is indicative of a recommendation to acquire a second set one or more images of the blood sample. The computer processor determines a characteristic of the blood sample by comparing the first set of one or more images to the second set of one or more images, and generates an output in response to the determined characteristic. Typically, the computer processor determines whether the entity is an extra-erythrocytic or an intra-erythrocytic entity, by comparing the first set of one or more images to the second set of one or more images, as described hereinabove.

There is therefore provided, in accordance with some applications of the present invention, a method for use with a blood sample that was drawn from a subject, the method including:

acquiring first and second images of the blood sample at respective times, using a microscope system; and using a computer processor:
determining whether between acquisitions of the first and second images there was relative motion between at least one erythrocyte within the sample and at least one entity within the sample, by comparing the first and second images to one another;
at least partially in response thereto, determining whether the entity is an extra-erythrocytic or an intra-erythrocytic entity; and
generating an output, at least partially in response thereto.

In some applications, the microscope system includes a microscope system that is disposed in a blood diagnosis machine that is accessible to the subject, and the method includes receiving the blood sample into the blood diagnosis machine by the subject placing the blood sample into a sample receiving unit of the blood diagnosis machine.

In some applications, acquiring first and second images of the blood sample includes acquiring first and second at least partially overlapping images of a portion of the blood sample.

In some applications, determining whether the entity is an extra-erythrocytic or an intra-erythrocytic entity includes determining whether the entity is an extra-erythrocytic or an intra-erythrocytic entity, at least partially based upon an amount of motion between the erythrocyte and the entity, and a time interval between acquisitions of the first and second images.

In some applications, determining whether the entity is an extra-erythrocytic or an intra-erythrocytic entity includes determining whether the entity is an extra-erythrocytic or an intra-erythrocytic entity, at least partially based upon an amount of motion between the erythrocyte and the entity, and an amount of agitation applied to the blood sample between acquisitions of the first and second images.

In some applications, determining whether the entity is an extra-erythrocytic or an intra-erythrocytic entity includes determining whether the entity is an extra-erythrocytic or an intra-erythrocytic entity, at least partially based upon an amount of motion between the erythrocyte and the entity, a time interval between acquisitions of the first and second images, and an amount of agitation applied to the blood sample between acquisitions of the first and second images.

In some applications, acquiring the first and second images of the blood sample at respective times includes acquiring the first image of the blood sample during a first scan of the blood sample in which a plurality of images of the blood sample are acquired from respective fields of view, and acquiring the second image of the blood sample during a second scan of the blood sample in which a plurality of images of the blood sample are acquired from respective fields of view.

In some applications, the method further includes preparing the blood sample in a monolayer, and acquiring the first and second images of the blood sample includes acquiring first and second images of the blood sample, while the blood sample is disposed in the monolayer.

In some applications, the method further includes, using the computer processor, at least partially based upon determining whether the entity is an extra-erythrocytic or an intra-erythrocytic entity, performing a blood count of the subject, and generating the output includes generating an indication of the blood count.

In some applications, the method further includes, using the computer processor, at least partially based upon determining whether the entity is an extra-erythrocytic or an intra-erythrocytic entity, diagnosing the subject as suffering from an intra-erythrocytic infection, and generating the output includes generating an indication of the diagnosis.

In some applications, the method further includes, using the computer processor, at least partially based upon determining whether the entity is an extra-erythrocytic or an intra-erythrocytic entity, diagnosing the subject as suffering from a medical condition, and generating the output includes generating an indication of the diagnosis.

In some applications, the method further includes staining the blood sample with a staining substance, and acquiring the first and second images includes acquiring the first and second images of the blood sample, while the blood sample is in a stained state.

In some applications, determining whether the entity is an extra-erythrocytic or an intra-erythrocytic entity includes determining whether the entity is a platelet.

In some applications, the method further includes, using the computer processor:
analyzing the first image;
based upon the analysis, identifying one or more entities within the first image that are disposed in a vicinity of the erythrocyte, and which have dimensions that indicate that the entities could be platelets; and
in response thereto, selecting to perform the comparing of the first image and the second image to one another.

In some applications, determining whether the entity is an extra-erythrocytic or an intra-erythrocytic entity includes determining that the entity is an intra-erythrocytic entity selected from the group consisting of: a Howell Jolly body, a reticular network of ribosomal DNA, a Heinz body, a Pappenheimer body, and a nucleus of a nucleated erythrocyte.

In some applications, determining whether the entity is an extra-erythrocytic or an intra-erythrocytic entity includes determining that the entity is an intra-erythrocytic parasite.

In some applications, determining that the entity is an intra-erythrocytic parasite includes determining that the entity is an intra-erythrocytic parasite selected from the group consisting of a *Plasmodium* parasite, and a *Babesia* parasite.

In some applications:
acquiring the first image of the blood sample includes acquiring a first set of images of the blood sample that includes a plurality of images;
acquiring the second image of the blood sample includes acquiring a second set of images of the blood sample that includes one or more images; and
comparing the first and second images to one another includes comparing one or more of the images belonging to the first set of images to respective images belonging to the second set of images.

In some applications, comparing one or more of the images belonging to the first set of images to respective images belonging to the second set of images includes comparing only some of the first set of images to respective images belonging to the second set of images, the method further including determining a characteristic of all of the blood sample based on the comparison.

In some applications, acquiring the second set of images includes imaging a portion of the blood sample that is smaller than a portion of the blood sample that was imaged by acquiring the first set of images.

In some applications, the method further includes:
analyzing the first set of images; and
based upon the analysis, selecting the portion of the blood sample to image in the second set of images.

In some applications, acquiring the first and second images of the blood sample at respective times includes acquiring the first and second images of the blood sample, a time interval between acquisitions of the first and second images being less than ten minutes.

In some applications, acquiring the first and second images of the blood sample at respective times includes acquiring the first and second images of the blood sample, the time interval between acquisitions of the first and second images being less than one minute.

In some applications, acquiring the first and second images of the blood sample at respective times includes acquiring the first and second images of the blood sample, the time interval between acquisitions of the first and second images being less than one second.

In some applications, the method further includes agitating the blood sample between acquisitions of the first and second images.

In some applications, agitating the blood sample includes placing magnetic beads inside the sample and moving the magnetic beads using an external magnetic field.

In some applications, agitating the blood sample includes moving a microscope stage upon which the blood sample is disposed.

There is further provided, in accordance with some applications of the present invention, a method for use with a blood sample that was drawn from a subject, the method including:
acquiring a first image of the blood sample, using a microscope system;
acquiring a second image of the blood sample, using the microscope system, there being a time interval between acquisitions of the first and second images; and
using a computer processor:
analyzing the first image of the blood sample;
at least partially in response thereto:
selecting to compare the first and second images of the blood sample to one another;
comparing the first and second images of the blood sample to one another; and
determining a characteristic of the blood sample, at least partially based upon comparing the first and second images of the blood sample to one another; and
generating an output in response to the determined characteristic.

In some applications, the microscope system includes a microscope system that is disposed in a blood diagnosis machine that is accessible to the subject, and the method includes receiving the blood sample into the blood diagnosis machine by the subject placing the blood sample into a sample receiving unit of the blood diagnosis machine.

In some applications, selecting to compare the first and second images of the blood sample to one another includes selecting to acquire the second image of the blood sample, and acquiring the second image of the blood sample includes automatically acquiring the second image in response thereto.

In some applications, acquiring the first and second images of the blood sample includes acquiring the first image of the blood sample during a first scan of the blood sample in which a plurality of images of the blood sample are acquired from respective fields of view, and acquiring the second image of the blood sample during a second scan of the blood sample in which a plurality of images of the blood sample are acquired from respective fields of view.

In some applications, the method further includes preparing the blood sample in a monolayer, and acquiring the first and second images of the blood sample includes acquiring the first and second images of the blood sample, while the blood sample is disposed in the monolayer.

In some applications, the method further includes staining the blood sample with a staining substance, and acquiring the first and second images of the blood sample includes acquiring the first and second images of the blood sample while the blood sample is in a stained state.

In some applications:
analyzing the first image includes identifying one or more entities within the first image that are disposed in a vicinity of an erythrocyte, and which have dimensions that indicate that the entities could be platelets, and
selecting to compare the first and second images of the blood sample to one another is performed at least partially in response thereto.

In some applications:
acquiring the first image of the blood sample includes acquiring a first set of images of the blood sample that includes a plurality of images;
acquiring the second image of the blood sample includes acquiring a second set of images of the blood sample that includes one or more images; and
selecting to compare the first and second images of the blood sample to one another includes selecting to compare at least a portion of the images belonging to the plurality of first images to respective images belonging to the plurality of second images.

In some applications, selecting to compare at least a portion of the images belonging to the plurality of first images to respective images belonging to the plurality of second images includes selecting to compare only some of the plurality of first images to respective images belonging to the plurality of second images, the method further including determining a characteristic of all of the blood sample based on comparing only some of the plurality of first images to respective images belonging to the plurality of second images.

In some applications, selecting to compare the first and second images of the blood sample to one another includes selecting to acquire the second set of images of the blood sample, the second set of images imaging a portion of the blood sample that is smaller than a portion of the blood sample that was imaged by acquiring the first set of images.

In some applications, determining a characteristic of the blood sample, at least partially based upon comparing the first and second images to one another includes:
determining whether between acquisitions of the first and second images, there was relative motion between at least one erythrocyte within the sample and at least one entity within the sample; and
at least partially in response thereto, determining whether the entity is an extra-erythrocytic or an intra-erythrocytic entity.

In some applications, determining whether the entity is an extra-erythrocytic or an intra-erythrocytic entity includes determining whether the entity is an extra-erythrocytic or an intra-erythrocytic entity, at least partially based upon an amount of motion between the erythrocyte and the entity, and the time interval between acquisitions of the first and second images.

In some applications, determining whether the entity is an extra-erythrocytic or an intra-erythrocytic entity includes determining whether the entity is an extra-erythrocytic or an intra-erythrocytic entity, at least partially based upon an amount of motion between the erythrocyte and the entity, and an amount of agitation applied to the blood sample between acquisitions of the first and second images.

In some applications, determining whether the entity is an extra-erythrocytic or an intra-erythrocytic entity includes determining whether the entity is an extra-erythrocytic or an intra-erythrocytic entity, at least partially based upon an amount of motion between the erythrocyte and the entity, the time interval between acquisitions of the first and second images, and an amount of agitation applied to the blood sample between acquisitions of the first and second images.

In some applications, the method further includes, using the computer processor, at least partially based upon determining whether the entity is an extra-erythrocytic or an intra-erythrocytic entity, performing a blood count of the subject, and generating the output includes generating an indication of the blood count.

In some applications, the method further includes, using the computer processor, at least partially based upon determining whether the entity is an extra-erythrocytic or an intra-erythrocytic entity, diagnosing the subject as suffering from an intra-erythrocytic infection, and generating the output includes generating an indication of the diagnosis.

In some applications, the method further includes, using the computer processor, at least partially based upon determining whether the entity is an extra-erythrocytic or an intra-erythrocytic entity, diagnosing the subject as suffering from a medical condition, and generating the output includes generating an indication of the diagnosis.

In some applications, determining whether the entity is an extra-erythrocytic or an intra-erythrocytic entity includes determining that the entity is a platelet.

In some applications, determining whether the entity is an extra-erythrocytic or an intra-erythrocytic entity includes determining that the entity is an intra-erythrocytic entity selected from the group consisting of: a Howell Jolly body, a reticular network of ribosomal DNA, a Heinz body, a Pappenheimer body, and a nucleus of a nucleated erythrocyte.

In some applications, determining whether the entity is an extra-erythrocytic or an intra-erythrocytic entity includes determining that the entity is an intra-erythrocytic parasite.

In some applications, determining that the entity is an intra-erythrocytic parasite includes determining that the entity is an intra-erythrocytic parasite selected from the group consisting of a *Plasmodium* parasite, and a *Babesia* parasite.

In some applications, acquiring the first and second images of the blood sample includes acquiring the first and second images of the blood sample, the time interval between acquisitions of the first and second images being less than ten minutes.

In some applications, acquiring the first and second images of the blood sample includes acquiring the first and second images of the blood sample, the time interval between acquisitions of the first and second images being less than one minute.

In some applications, acquiring the first and second images of the blood sample includes acquiring the first and second images of the blood sample, the time interval between acquisitions of the first and second images being less than one second.

In some applications, the method further includes agitating the blood sample between acquisitions of the first and second images.

In some applications, agitating the blood sample includes placing magnetic beads inside the sample and moving the magnetic beads using an external magnetic field.

In some applications, agitating the blood sample includes moving a microscope stage upon which the blood sample is disposed.

There is further provided, in accordance with some applications of the present invention, apparatus for use with an output device, and a blood sample that was drawn from a subject, the apparatus including:

a microscope system configured to acquire first and second images of the blood sample at respective times; and a computer processor configured to:
  determine whether, between acquisitions of the first and second images, there was relative motion between at least one erythrocyte within the sample and at least one entity within the sample, by comparing the first and second images to one another,
  at least partially in response thereto, determine whether the entity is an extra-erythrocytic or an intra-erythrocytic entity, and
  generate an output on the output device, at least partially in response thereto.

In some applications, the microscope system includes a microscope system that is disposed in a blood diagnosis machine, the apparatus further including a sample receiving unit configured to receive the blood sample into the blood diagnosis machine by the subject placing the blood sample into the sample receiving unit.

In some applications, the microscope system is configured to acquire the first and second images of the blood sample by acquiring first and second at least partially overlapping images of a portion of the blood sample.

In some applications, the computer processor is configured to determine whether the entity is an extra-erythrocytic or an intra-erythrocytic entity, at least partially based upon an amount of motion between the erythrocyte and the entity, and a time interval between acquisitions of the first and second images.

In some applications, the computer processor is configured to determine whether the entity is an extra-erythrocytic or an intra-erythrocytic entity, at least partially based upon an amount of motion between the erythrocyte and the entity, and an amount of agitation applied to the blood sample between acquisitions of the first and second images.

In some applications, the computer processor is configured to determine whether the entity is an extra-erythrocytic or an intra-erythrocytic entity, at least partially based upon an amount of motion between the erythrocyte and the entity, a time interval between acquisitions of the first and second images, and an amount of agitation applied to the blood sample between acquisitions of the first and second images.

In some applications, the microscope system is configured to acquire the first and second images of the blood sample at respective times by acquiring the first image of the blood sample during a first scan of the blood sample in which a plurality of images of the blood sample are acquired from respective fields of view, and acquiring the second image of the blood sample during a second scan of the blood sample in which a plurality of images of the blood sample are acquired from respective fields of view.

In some applications, the computer processor is configured to perform a blood count of the subject, at least partially based upon determining whether the entity is an extra-erythrocytic or an intra-erythrocytic entity, and the computer processor is configured to generate the output by generating an indication of the blood count.

In some applications, the computer processor is configured to diagnose the subject as suffering from an intra-erythrocytic infection, at least partially based upon determining whether the entity is an extra-erythrocytic or an intra-erythrocytic entity, and the computer processor is configured to generate the output by generating an indication of the diagnosis.

In some applications, the computer processor is configured to diagnose the subject as suffering from a medical condition, at least partially based upon determining whether the entity is an extra-erythrocytic or an intra-erythrocytic entity, and the computer processor is configured to generate the output by generating an indication of the diagnosis.

In some applications, the apparatus further includes a staining substance configured to stain the blood sample, and the microscope system is configured to acquire the first and second images by acquiring the first and second images of the blood sample, while the blood sample is in a stained state.

In some applications, the computer processor is configured to determine whether the entity is a platelet, at least partially based upon determining whether the entity is an extra-erythrocytic or an intra-erythrocytic entity.

In some applications, the computer processor is configured to:
  analyze the first image;
  based upon the analysis, identify one or more entities within the first image that are disposed in a vicinity of the erythrocyte, and which have dimensions that indicate that the entities could be platelets; and
  in response thereto, select to perform the comparing of the first image and the second image to one another.

In some applications, the computer processor is configured to determine whether the entity is an intra-erythrocytic entity selected from the group consisting of: a Howell Jolly body, a reticular network of ribosomal DNA, a Heinz body, a Pappenheimer body, and a nucleus of a nucleated erythrocyte, at least partially based upon determining whether the entity is an extra-erythrocytic or an intra-erythrocytic entity.

In some applications, the computer processor is configured to determine that the entity is an intra-erythrocytic parasite, at least partially based upon determining whether the entity is an extra-erythrocytic or an intra-erythrocytic entity.

In some applications, the computer processor is configured to determine that the entity is an intra-erythrocytic parasite selected from the group consisting of a *Plasmodium* parasite, and a *Babesia* parasite.

In some applications:
  the microscope system is configured to acquire the first image of the blood sample by acquiring a first set of images of the blood sample that includes a plurality of images;

the microscope system is configured to acquire the first image of the blood sample by acquiring a second set of images of the blood sample that includes one or more images; and the computer processor is configured to compare the first and second images to one another by comparing one or more of the images belonging to the first set of images to respective images belonging to the second set of images.

In some applications, the computer processor is configured to compare only some of the first set of images to respective images belonging to the second set of images, and to determine a characteristic of all of the blood sample based on the comparison.

In some applications, the microscope system is configured to acquire the second set of images by imaging a portion of the blood sample that is smaller than a portion of the blood sample that was imaged by acquiring the first set of images.

In some applications, the computer processor is configured to:

analyze the first set of images; and based upon the analysis, select the portion of the blood sample to image in the second set of images.

In some applications, the microscope system is configured to acquire the first and second images of the blood sample, a time interval between acquisitions of the first and second images being less than ten minutes.

In some applications, the microscope system is configured to acquire the first and second images of the blood sample, the time interval between acquisitions of the first and second images being less than one minute.

In some applications, the microscope system is configured to acquire the first and second images of the blood sample, the time interval between acquisitions of the first and second images being less than one second.

In some applications, the computer processor is configured to generate agitation of the blood sample between acquisitions of the first and second images.

In some applications, the apparatus further includes magnetic beads configured to be placed inside the sample, and the computer processor is configured to move the magnetic beads by controlling an external magnetic field.

In some applications, the computer processor is configured to generate agitation of the sample by moving a microscope stage upon which the blood sample is disposed.

There is further provided, in accordance with some applications of the present invention, apparatus for use with a blood sample that was drawn from a subject and an output device, the apparatus including:

a microscope system configured to acquire:
a first image of the blood sample, using a microscope system, and
a second image of the blood sample, there being a time interval between acquisitions of the first and second images; and
a computer processor configured to:
analyze the first image of the blood sample,
at least partially in response thereto:
select to compare the first and second images of the blood sample to one another,
compare the first and second images of the blood sample to one another, and
determine a characteristic of the blood sample, at least partially based upon comparing the first and second images of the blood sample to one another, and
generate an output in response to the determined characteristic.

In some applications, the microscope system includes a microscope system that is disposed in a blood diagnosis machine, the apparatus further including a sample receiving unit configured to receive the blood sample into the blood diagnosis machine by the subject placing the blood sample into the sample receiving unit.

In some applications, the computer processor, in selecting to compare the first and second images of the blood sample to one another, is configured to select to acquire the second image of the blood sample, and is configured to automatically drive the microscope system to acquire the second image, in response thereto.

In some applications, the microscope system is configured to acquire the first and second images of the blood sample by acquiring the first image of the blood sample during a first scan of the blood sample in which a plurality of images of the blood sample are acquired from respective fields of view, and acquiring the second image of the blood sample during a second scan of the blood sample in which a plurality of images of the blood sample are acquired from respective fields of view.

In some applications, the apparatus further includes a staining substance configured to stain the blood sample, and the microscope system is configured to acquire the first and second images by acquiring the first and second images of the blood sample, while the blood sample is in a stained state.

In some applications, the computer processor is configured:

to identify one or more entities within the first image that are disposed in a vicinity of an erythrocyte, and which have dimensions that indicate that the entities could be platelets, by analyzing the first image, and to select to compare the first and second images of the blood sample to one another at least partially in response thereto.

In some applications:

the microscope system is configured to acquire the first image of the blood sample by acquiring a first set of images of the blood sample that includes a plurality of images;

the microscope system is configured to acquire the second image of the blood sample by acquiring a second set of images of the blood sample that includes one or more images; and the computer processor is configured to select to compare at least a portion of the images belonging to the plurality of first images to respective images belonging to the plurality of second images.

In some applications, the computer processor is configured to select to compare only some of the plurality of first images to respective images belonging to the plurality of second images, and is configured to determine a characteristic of all of the blood sample based on comparing only some of the plurality of first images to respective images belonging to the plurality of second images.

In some applications, the computer processor, in selecting to compare the first and second images of the blood sample to one another, is configured to select to acquire the second set of images of the blood sample, the second set of images imaging a portion of the blood sample that is smaller than a portion of the blood sample that was imaged by acquiring the first set of images.

In some applications, the computer processor is configured to determine a characteristic of the blood sample, at least partially based upon comparing the first and second images to one another by:

determining whether between acquisitions of the first and second images, there was relative motion between at least one erythrocyte within the sample and at least one entity within the sample; and at least partially in response thereto, determining whether the entity is an extra-erythrocytic or an intra-erythrocytic entity.

In some applications, the computer processor is configured to determine whether the entity is an extra-erythrocytic or an intra-erythrocytic entity, at least partially based upon an amount of motion between the erythrocyte and the entity, and the time interval between acquisitions of the first and second images.

In some applications, the computer processor is configured to determine whether the entity is an extra-erythrocytic or an intra-erythrocytic entity, at least partially based upon an amount of motion between the erythrocyte and the entity, and an amount of agitation applied to the blood sample between acquisitions of the first and second images.

In some applications, the computer processor is configured to determine whether the entity is an extra-erythrocytic or an intra-erythrocytic entity, at least partially based upon an amount of motion between the erythrocyte and the entity, the time interval between acquisitions of the first and second images, and an amount of agitation applied to the blood sample between acquisitions of the first and second images.

In some applications, the computer processor is configured to perform a blood count of the subject, at least partially based upon determining whether the entity is an extra-erythrocytic or an intra-erythrocytic entity, and the computer processor is configured to generate the output by generating an indication of the blood count.

In some applications, the computer processor is configured to diagnose the subject as suffering from an intra-erythrocytic infection, at least partially based upon determining whether the entity is an extra-erythrocytic or an intra-erythrocytic entity, and the computer processor is configured to generate the output by generating an indication of the diagnosis.

In some applications, the computer processor is configured to diagnose the subject as suffering from a medical condition, at least partially based upon determining whether the entity is an extra-erythrocytic or an intra-erythrocytic entity, and the computer processor is configured to generate the output by generating an indication of the diagnosis.

In some applications, the computer processor is configured to determine whether the entity is a platelet, at least partially based upon determining whether the entity is an extra-erythrocytic or an intra-erythrocytic entity.

In some applications, the computer processor is configured to determine whether the entity is an intra-erythrocytic entity selected from the group consisting of: a Howell Jolly body, a reticular network of ribosomal DNA, a Heinz body, a Pappenheimer body, and a nucleus of a nucleated erythrocyte, at least partially based upon determining whether the entity is an extra-erythrocytic or an intra-erythrocytic entity.

In some applications, the computer processor is configured to determine whether the entity is an intra-erythrocytic parasite, at least partially based upon determining whether the entity is an extra-erythrocytic or an intra-erythrocytic entity.

In some applications, the computer processor is configured to determine that the entity is an intra-erythrocytic parasite selected from the group consisting of a *Plasmodium* parasite, and a *Babesia* parasite, at least partially based upon determining whether the entity is an extra-erythrocytic or an intra-erythrocytic entity.

In some applications, the microscope system is configured to acquire the first and second images of the blood sample, the time interval between acquisitions of the first and second images being less than ten minutes.

In some applications, the microscope system is configured to acquire the first and second images of the blood sample, the time interval between acquisitions of the first and second images being less than one minute.

In some applications, the microscope system is configured to acquire the first and second images of the blood sample, the time interval between acquisitions of the first and second images being less than one second.

In some applications, the computer processor is configured to generate agitation of the blood sample between acquisitions of the first and second images.

In some applications, the apparatus further includes magnetic beads configured to be placed inside the sample, and the computer processor is configured to move the magnetic beads by controlling an external magnetic field.

In some applications, the computer processor is configured to generate agitation of the sample by moving a microscope stage upon which the blood sample is disposed.

There is further provided, in accordance with some applications of the present invention, a computer software product, for use with a blood sample that was drawn from a subject, and a microscope system configured to acquire first and second images of the blood sample at respective times, the computer software product including a non-transitory computer-readable medium in which program instructions are stored, which instructions, when read by a computer cause the computer to perform the steps of: determining whether between acquisitions of the first and second images there was relative motion between at least one erythrocyte within the sample and at least one entity within the sample, by comparing the first and second images to one another; at least partially in response thereto, determining whether the entity is an extra-erythrocytic or an intra-erythrocytic entity; and generating an output, at least partially in response thereto.

There is further provided, in accordance with some applications of the present invention, a computer software product, for use with a blood sample that was drawn from a subject, and a microscope system configured to acquire a first and image of the blood sample and a second image of the blood sample, there being a time interval between acquisitions of the first and second images, the computer software product including a non-transitory computer-readable medium in which program instructions are stored, which instructions, when read by a computer cause the computer to perform the steps of: analyzing the first image of the blood sample; at least partially in response thereto: selecting to compare the first and second images of the blood sample to one another; comparing the first and second images of the blood sample to one another; and determining a characteristic of the blood sample, at least partially based upon comparing the first and second images of the blood sample to one another; and generating an output in response to the determined characteristic.

The present invention will be more fully understood from the following detailed description of applications thereof, taken together with the drawings, in which:

BRIEF DESCRIPTION OF THE DRAWINGS

FIGS. 2A-B are first and second images of a *Plasmodium* parasite within an erythrocyte, a time interval having passed between acquisitions of the first and second images, the images having been acquired in accordance with some applications of the present invention;

FIGS. 3A-B are first and second images of a platelet in the vicinity of an erythrocyte, a time interval having passed between acquisitions of the first and second images, the images having been acquired in accordance with some applications of the present invention;

DETAILED DESCRIPTION OF EMBODIMENTS

Figure 1:
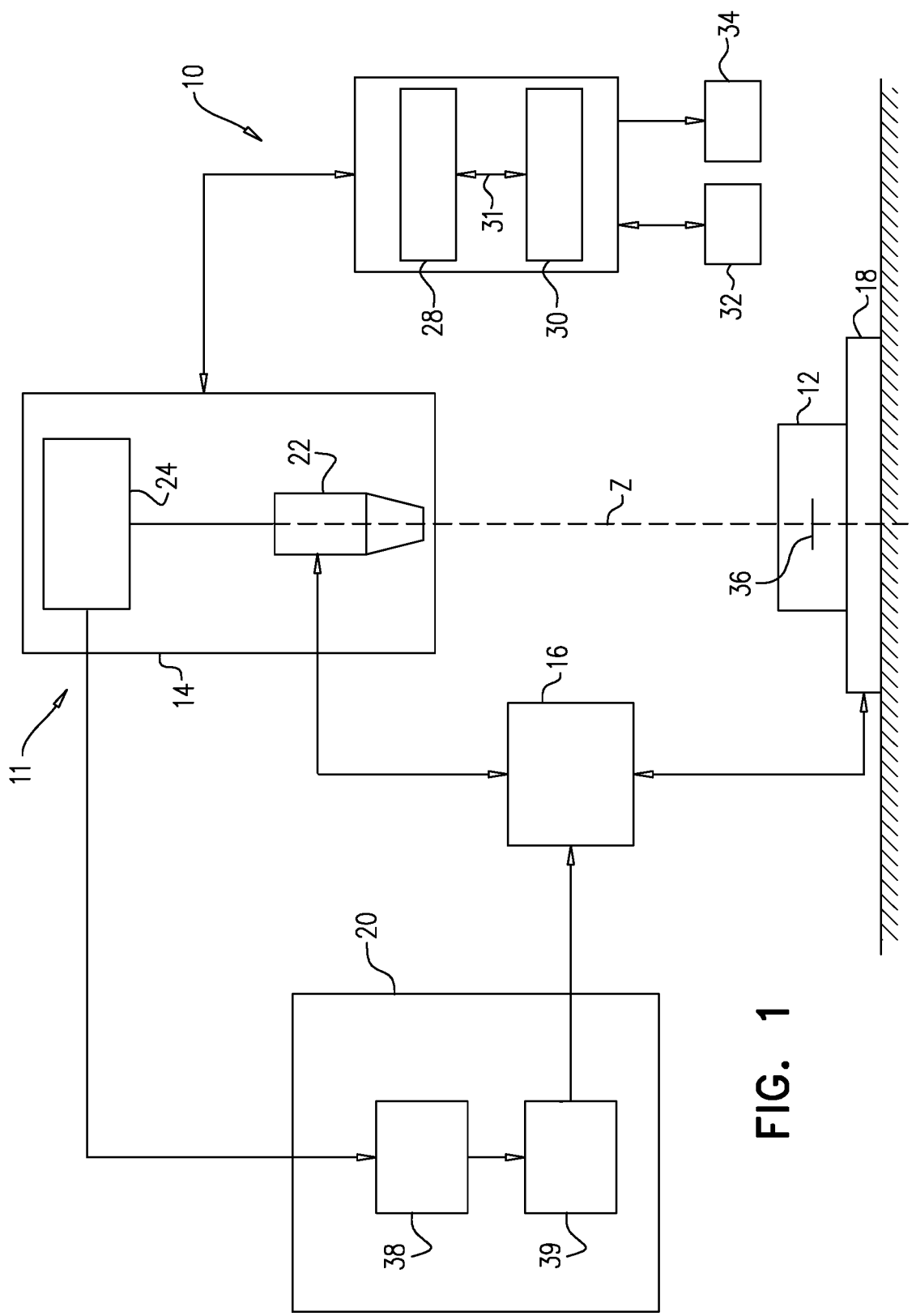
FIG. 1 is a schematic illustration of a microscope system that is used for analyzing a cell sample, in accordance with some applications of the present invention.

Reference is now made to FIG. 1, which is a schematic illustration of a microscope system 10 that is used for analyzing a cell sample (e.g., a blood sample) 12, in accordance with some applications of the present invention. Typically, microscope system 10 includes an imaging module 14, a focus variation module 16, a sample carrier 18 and an autofocus system 20. For some applications, the microscope system is generally similar to the microscope system described in US 2014/0347459 to Greenfield, which is incorporated herein by reference. Cell sample 12 is typically a blood sample that is prepared such as to form a monolayer within which cells are not fixed in position, for example, using techniques as described in PCT Application Publication WO 15/001553 to Pollack, which is incorporated herein by reference.

Imaging module 14 acts as an imaging device. Typically, imaging module 14, which acts as an imaging device, includes an optical unit 22 and an image sensor unit 24. Optical unit 22 is configured to form a magnified image of a sample (for example, cell sample 12) by conjugating a focus plane 36 and an image plane. The image sensor unit 24 typically includes an image sensor, for example a charge-coupled-device (CCD), complementary metal-oxide-semiconductor (CMOS) sensor, and/or a matrix sensor, positioned in the image plane of the optical unit 22 so as to sense the magnified image.

A computer processor 28 typically receives and processes images. The computer processor communicates with a memory 30. Via a user interface 32, a user (e.g., a laboratory technician) sends instructions to the computer processor. For some applications, the user interface includes a keyboard, a mouse, a joystick, a touchscreen device (such as a smartphone or a tablet computer), a touchpad, a trackball, a voice-command interface, and/or other types of user interfaces that are known in the art. Typically, the computer processor generates an output via an output device 34. Further typically, the output device includes a display, such as a monitor, and the output includes an output that is displayed on the display. For some applications, the processor generates an output on a different type of visual, text, graphics, tactile, audio, and/or video output device, e.g., speakers, headphones, a smartphone, or a tablet computer. For some applications, user interface 32 acts as both an input device and an output device. For some applications, the processor generates an output on a computer-readable medium (e.g., a non-transitory computer-readable medium), such as a disk, or a portable USB drive, and/or generates an output on a printer.

Image sensor unit 24 may output acquired digital images to output device 34 (which may include a display) and/or to the autofocus system 20. Focus variation module 16 may be configured to vary a distance between the focus plane 36 of the optical unit 22 and the sample carrier 18. Focus variation module 16 may be operated manually or automatically via a mechanical interface which may, for example, modify the position of the sample carrier 18 along an optical axis Z of the optical unit 22. Alternatively or additionally, focus variation module 16 may be commanded by autofocus system 20. For example, the focus variation module 16 may vary the distance between the sample carrier 18 and the focus plane by (1) modifying the position of optical unit 22 along the optical axis Z, (2) modifying the position of the sample carrier 18 along the position of the optical axis Z (e.g., by moving a stage upon which the sample carrier is placed), (3) modifying the position of the focus plane by, for example, changing a focal length of the optical unit 22, or a combination thereof.

The sample carrier 18 may comprise a plate, which is typically placed on a stage of the microscope system. Sample carrier 18 may be configured to accommodate cell sample 12. The carrier may be any carrier known in the art for holding a biological sample. Optionally, the bottom surface of the carrier is essentially flat, to allow cells in contact therewith to be at about the same distance from the focal plane of the microscope. Examples include carrier slides, laboratory receptacles, dishes, plates, multi-well plates, test tubes (e.g. with a flat bottom), microfluidic cells and cartridges and the like. Typically, the sample carrier is similar to that described in PCT Application Publication WO 15/001553 to Pollack, which is incorporated herein by reference. For some applications, a cell suspension comprising red blood cells is introduced onto a base surface of a carrier having a vertical height being greater than or equal to a vertical depth of said cell suspension when on the base carrier. The cells in the cell suspension are allowed to settle (without applying any force thereon) on the base surface of the carrier to form a monolayer of cells on the base surface of the carrier, without fixing the cells in position. Optionally, the solution has a vertical height of between 20 micrometers and 1,000 micrometers.

The blood sample that is imaged is typically raw blood, or a portion of raw blood that includes at least red blood cells, in diluted or undiluted form. Optionally, the blood sample is a cell sample derived from the human body, the sample including at least red blood cells, and is optionally modified by addition and/or removal of cells and/or other components. Typically, images are acquired of a portion of a blood sample that has been drawn from a subject's body. For example, the sample that is drawn from the subject's body may be divided between a plurality of sample carriers, within each of which monolayers are allowed to form (e.g., using techniques as described in PCT Application Publication WO 15/001553 to Pollack, which is incorporated herein by reference). Images may be acquired of sample carrier 18 or a portion thereof. For example, each of the sample carriers may be scanned, such that a plurality of images of the carrier are acquired, from respective fields of vision at respective locations along the bottom surface of sample carrier 18.

For some applications, one or more staining substances are used to stain the sample before the sample is imaged. For example, the staining substance may be configured to stain DNA with preference over staining of other cellular components. Alternatively, the staining substance may be configured to stain all cellular nucleic acids with preference over staining of other cellular components. For example, the sample may be stained with acridine orange reagent, Hoechst reagent, and/or any other staining substance that is configured to preferentially stain DNA and/or RNA within the blood sample. Optionally, the staining substance is configured to stain all cellular nucleic acids but the staining of DNA and RNA are each more prominently visible under some lighting and filter conditions, as is known, for example, for acridine orange. Images of the sample may be acquired using imaging conditions that allow detection of cells (e.g., bright-field) and/or imaging conditions that allow visualization of stained bodies (e.g. appropriate fluorescent illumination).

For some applications, the methods described herein are performed without staining the blood sample. For example, when the methods described herein are performed in order to determine a platelet count, the blood sample may be imaged without staining the blood sample.

Autofocus system 20 may comprise an autofocus computation module 38 and an autofocus adaption module 39. The autofocus computation module may be connected to the image sensor unit 24 so as to receive images acquired by the imaging module 14. The autofocus adaptation module may be connected to the focus variation module 16 and may be configured to command the focus variation module 16, e.g., as described above.

In accordance with some applications, a blood sample is scanned by the microscope system, such that a plurality of portions of the blood sample are imaged. For some applications, a plurality of images are acquired of one or more portions of the blood sample, with each of the plurality of images being acquired under respective imaging conditions. For example, two images of a portion of the sample may be acquired using, respectively, imaging conditions that allow detection of cells (e.g., bright-field) and imaging conditions that allow visualization of stained bodies (e.g. appropriate fluorescent illumination).

Reference is now made to FIGS. 2A-B, which are first and second images of a *Plasmodium* parasite 40 (which appears as a bright speck) within an erythrocyte 42, a time interval of approximately 5 minutes having passed between acquisitions of the first and second images, the images having been acquired in accordance with some applications of the present invention. Reference is also made to FIGS. 3A-B, which are first and second images of a platelet 44 (which also appears as a bright speck) in the vicinity of an erythrocyte 46, a time interval of approximately 5 minutes having passed between acquisitions of the first and second images, the images having been acquired in accordance with some applications of the present invention.

The images shown in FIGS. 2A-B and 3A-B are of monolayers of diluted blood samples that were stained with fluorescent nucleic acid stains and were imaged at 20 times magnification. The samples were placed in sample carriers, which were scanned such that 180 fields of vision of each sample carrier were imaged. The samples were scanned twice, such that each field was re-imaged after a time interval of approximately 5 minutes had passed since the previous image of that field. During scanning, the samples were gently moved together with the microscope stage so that each field of vision was disposed, in turn, under the microscope objective lens for imaging. Images were acquired using bright-field imaging, as well as fluorescent imaging. Each of the images shown in FIGS. 2A-B and 3A-B shows the fluorescent intensity overlaid on a bright-field image.

As may be observed by comparing the transition from FIG. 2A to 2B, to the transition from FIG. 3A to FIG. 3B, it was found that there is relative motion between platelets and erythrocytes within the sample. In general, it was found that, while both platelets and erythrocytes typically moved in the order of tens of microns or less, platelets underwent greater movement than the erythrocytes. Thus, when two images, the acquisitions of which were separated by a time interval (e.g., as was the case for the images shown in FIGS. 3A and 3B) were compared to one another, platelets moved relative to a nearby or overlapping erythrocyte. By contrast, as shown in FIGS. 2A and 2B, *Plasmodium* parasites within infected erythrocytes did not move substantially with respect to the erythrocytes. Only in very rare events does *Plasmodium* separate from an essentially intact erythrocyte in which the *Plasmodium* is disposed.

As stated above, the images shown in FIGS. 2A-B and 3A-B were generated when the sample carrier was gently moved together with a microscope stage, in order to image a plurality of fields of vision along the sample. However, relative motion of platelets with respect to erythrocytes was evident, even when the sample was not moved between the acquisitions of respective images. Movement of the platelets relative to erythrocytes may be enhanced by moving the sample carrier, agitating the sample carrier, and/or vibrating the sample carrier. Therefore, for some applications of the present invention, a sample carrier is moved, agitated, or vibrated between acquisitions of respective images of the sample. Alternatively or additionally, the sample is stirred using magnetic beads disposed within the sample, and an external magnetic field that drives the magnetic beads to move.

Motion of platelets with respect to erythrocytes relative that of intracellular parasites is detectable within a short time period, such as less than 10 minutes, 7 minutes, or 5 minutes. In some cases, motion of platelets with respect to erythrocytes relative that of intracellular parasites is detectable within less than 1 minute, less than 10 seconds, or less than 1 second, the extent of the motion depending on the conditions that are used. Therefore, for some applications of the present invention, first and second images that are separated by a time interval of less than 10 minutes, less than 7 minutes, less than 5 minutes, less than 1 minute, less than 10 seconds, or less than 1 second are compared to one another. Typically, the difference between the motion of platelets with respect to erythrocytes relative that of intracellular parasites is dependent upon the time interval between image acquisitions, and/or the extent to which the sample carrier is agitated between image acquisitions.

It was found that the above-described effect is evident even if there is a time interval of several hours between when the sample is prepared, and when the first image is acquired. Within this time period drying effects of the blood are not detrimental to the above-described effect. Therefore, for some applications, techniques as described herein are performed on a blood sample, even several hours (e.g., up to five hours) from when the blood sample is prepared.

Figure 4:
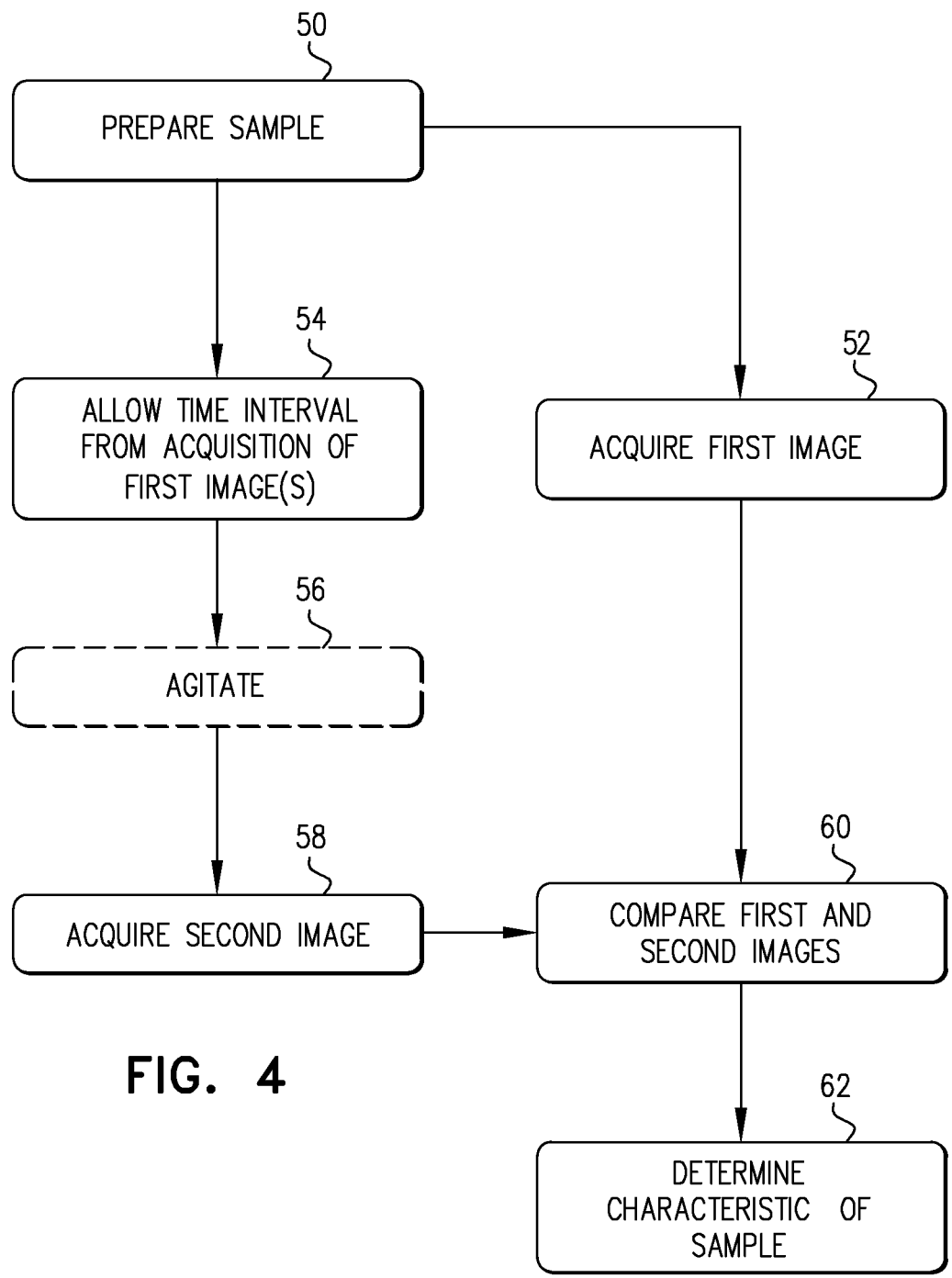
FIG. 4 is a flowchart showing steps of a procedure for analyzing a blood sample, in accordance with some applications of the present invention.

Reference is now made to FIG. 4, which is flowchart showing steps of a procedure that is performed, in accordance with some applications of the present invention.

In a first step 50, the blood sample is prepared, for example, in sample carrier 18 (schematically shown in FIG.

1). The blood sample is typically raw blood, or a portion of raw blood that includes at least red blood cells, optionally in diluted form. Optionally, the blood sample is a cell sample derived from the human body, the sample including at least red blood cells, and optionally modified by addition and/or removal of cells and/or other components. Typically, the blood sample is in a preparation within which erythrocytes and other entities within the sample are not maintained in fixed positions. For example, the blood sample may be prepared by allowing the sample to form a monolayer, as described, for example, in PCT Application Publication WO 15/001553 to Pollack, which is incorporated herein by reference. Preparing the sample in this manner facilitates motion of bodies within the sample with respect to one another. For some applications, a sample that is drawn from the subject's body is divided between a plurality of sample carriers, within each of which monolayers are allowed to form.

In step 52, a first image of the sample is acquired, typically using microscope system 10. A time interval from the acquisition of the first image is allowed to pass (step 54). For some applications, the time interval is less than 10 minutes, less than 7 minutes, less than 5 minutes, less than 1 minute, less than 10 seconds, and/or less than 1 second. Optionally, during this period the sample is agitated (step 56, which is in a dashed box to indicate that this step is optional). For example, the sample carrier may be moved, or vibrated, and/or magnetic beads may be used to stir the sample, as described hereinabove. After the time interval has passed, a second image of the sample is acquired (step 58), typically using the microscope system.

It is noted that, typically, first and second sets of images are acquired, with images from the second set of images typically at least partially overlapping with corresponding images from the first set of images. As such, steps of the procedure that are described as being performed with respect to first and second images are typically performed with respect to a plurality of first images, and a plurality of second images. For example, the sample carrier may be scanned twice in sequence, such that first and second images of the sample are acquired from a plurality of fields of view. The first and second scans may be performed, for example, in the same direction as one another (i.e., such that the order in which the fields of view are imaged in the first and second scans is the same), or in reverse from one another (i.e., such that, in the second scan, the fields of view are imaged in the reverse order from the first scan). Optionally, one or both of the first and second scans is performed in a random order, and/or the order in which the fields of view are imaged (at least in the second scan) is such as to minimize the time needed to acquire all needed images. For some applications, the time interval between acquisitions of first and second images of a field of view is determined by the scanning speed of the microscope system (i.e., the time that it takes the system to arrive back at the field of view in order to image the field of view for a second time). For some applications, first and second images of a field of view are acquired without the microscope system acquiring images of any additional fields of view between the acquisitions of the first and second images.

For some applications, the image or the second set of images is acquired only after analysis of the first image, or first set of images, or a portion thereof, indicates that it is desirable to acquire a second image or second set of images (e.g., as described herein). For some such applications, only a portion of fields of view are re-imaged (for example, a plurality of first images and only one second image may be acquired), and/or at least some of the images that are acquired during a second scan may be acquired at a different magnification from that of images acquired during the first scan.

In step 60, the first and second images are compared to one another. Typically, computer processor identifies one or more entities having dimensions and/or other characteristics that are such that the entity is a platelet candidate (i.e., an entity that could potentially be a platelet), and/or an intra-erythrocytic-parasite candidate (i.e., an entity that could potentially be an intra-erythrocytic-parasite, such as *Plasmodium*, and/or *Babesia*). Typically, the entity is an entity the dimensions or other characteristics of which (e.g., the location of which with respect to an erythrocyte), are such that the entity appears to be either a platelet or an intra-erythrocytic parasite, and it is unclear which of the two it is.

In step 62, the computer processor determines a characteristic of the blood sample based at least in part upon the comparison of the first and second images to one another. For example, in response to determining that (a) in the first image the entity is disposed in the vicinity of an erythrocyte, and that (b) there was relative motion between the erythrocyte and the entity between acquisitions of the first and second images (e.g., relative motion of at least one micron), the computer processor may confirm that the entity is a platelet. Alternatively, in response to determining that (a) in the first image the entity is disposed in the vicinity of an erythrocyte, and that (b) there was little or no relative motion between the erythrocyte and the entity between acquisitions of the first and second images, the computer processor may determine that the entity is an intra-erythrocytic entity. Based at least in part upon determining that the entity is an intra-erythrocytic entity, the computer processor may determine that the entity is an intra-erythrocytic parasite, such as *Plasmodium*, and/or *Babesia*.

Alternatively or additionally, based at least in part upon determining whether the entity is an intra-erythrocytic entity or an extra-erythrocytic entity, the computer processor may perform a blood sample analysis. For example, the computer processor may perform a complete blood count, which includes a count of platelets that takes into account whether the entity is an extra-erythrocytic entity (and therefore a platelet) or an intra-erythrocytic entity.

For some applications, the computer processor does not necessarily determine whether or not the entity is an intra-erythrocytic entity or an extra-erythrocytic entity, but rather determines the likelihood of the entity being one or the other of these, and performs analysis of the blood sample based upon the determined likelihood.

For some applications, in performing steps 60 and 62, the computer processor runs an algorithm that accounts for the time interval between acquisitions of the first and second images, and/or data indicative of agitation of the sample (e.g., the extent of its motion with the microscope stage).

Typically, if the computer processor identifies that an entity that (based upon the first image) was an intra-erythrocytic candidate, is no longer associated with the same erythrocyte (in the second image), or if there is no intra-erythrocytic candidate in the vicinity of the original location of the candidate, then the computer processor determines that the candidate is not an intra-erythrocytic entity, and/or that the candidate is not a parasite. For some applications, movement of an intra-erythrocytic candidate relative to the movement of an erythrocyte is used to filter out non-parasites from a parasite count, and/or to enhance confidence in a count of malaria parasites (e.g., utilizing a machine learning statistical algorithm).

For some applications, a blood sample contains a plurality of entities which may be intra-erythrocytic entities, or may be platelets. Some fields of view are re-imaged using the techniques described herein, in order to re-image some or all of the entities which may be intra-erythrocytic entities, or may be platelets. Based upon the number of such entities that are determined to be either platelets or intra-erythrocytic parasites, the computer processor estimates the number of such entities within the whole sample that are platelets and the number of such entities that are intra-erythrocytic parasites.

For some applications, the computer processor uses the determination of whether the entity is an intra-erythrocytic entity or an extra-erythrocytic entity as data in blood sample analysis e.g., in order to perform a complete blood count, or a portion thereof. For such applications, the computer processor may utilize the techniques described herein to correct the platelet count, by accounting for platelets that may not otherwise have been identified as platelets, due to platelets being disposed in the vicinity of erythrocytes. In addition, the computer processor may use the techniques described herein to identify certain intra-erythrocytic entities, which might otherwise not have been identified as such, due to being confused with platelets. For example, the computer processor may utilize the techniques described herein to identify Howell Jolly bodies, reticular networks of ribosomal DNA of reticulocytes, Heinz bodies, Pappenheimer bodies, and/or nuclei of nucleated erythrocytes, inter alia, by distinguishing between such entities and platelets. Reticulocytes are immature erythrocytes having reticular networks of ribosomal DNA, while nucleated erythrocytes are immature erythrocytes having a nucleus. These intracellular organelles, which do not exist in mature erythrocytes, may sometimes appear similar to platelets.

Figure 5:
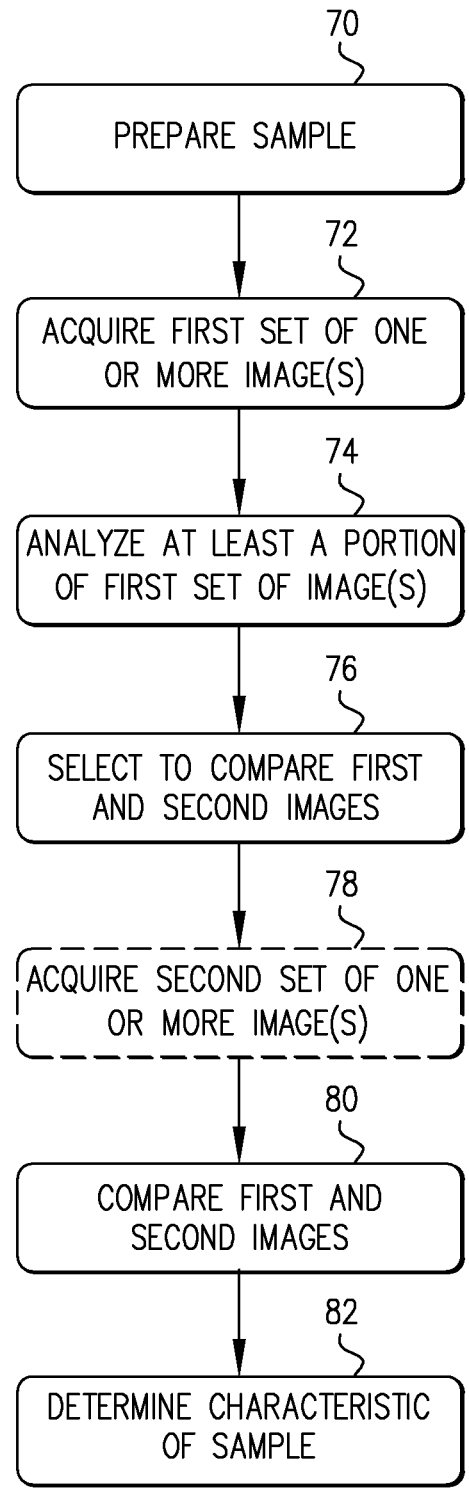
FIG. 5 is a flowchart showing steps of a procedure for analyzing a blood sample, in accordance with some applications of the present invention.

Reference is now made to FIG. 5, which is flowchart showing steps of a procedure that is performed, in accordance with some applications of the present invention. In a first step 70, the blood sample is prepared, for example, in sample carrier 18 (shown schematically in FIG. 1). Step 70 is typically generally similar to step 50 described with reference to FIG. 4. In a second step 72, a first set of one or more images of the sample is acquired. Step 72 is typically generally similar to step 52 described with reference to FIG. 4. As described hereinabove, an image from a single field of view may be acquired, or the sample carrier may be scanned such that a plurality of images are acquired from respective fields of view.

In step 74, the first set of image(s) is analyzed. In step 76, based upon the analysis of the first set of images, the computer processor selects whether it is desirable to compare images belonging to the first set of images to images belonging to a second set of images. For example, the computer processor may determine that within one or more of the first set of images there are one or more platelet candidates and/or one or more *Plasmodium* candidates and/or one or more *Babesia* candidates that overlap with an erythrocyte. In response to the analysis, the computer processor may automatically acquire a second set of one or more images of the blood sample (step 78), and/or may generate an output (e.g., on output device 34, shown in FIG. 1) indicative of a recommendation to acquire a second set one or more images of the blood sample.

It is noted that FIG. 5 indicates that the computer processor acquires a second set of images (step 78), based upon analyzing the first set of images. However, for some applications, even without having analyzed the first set of images, the computer processor automatically drives the microscope system to acquire a second set of images. For example, the computer processor may drive the microscope system to scan a sample carrier twice. For such applications, in step 76, subsequent to having acquired both sets of images, the computer processor selects whether or not it is desirable to compare the images belonging to the first set to images belonging to the second set, and then proceeds directly to comparing the images, in step 80.

It is noted that, in general, the steps of the flowchart shown in the figures (e.g., FIGS. 4 and 5) are not necessarily performed in the sequence in which they are shown. For example, with reference to FIG. 5, for some applications, step 78 is performed before step 72 is terminated, such that images belonging to both the first and second sets are acquired simultaneously and/or alternately with respect to one another. For example, once at least one image of the first set is acquired (step 72), it may be analyzed (step 74) and a selection may be made to compare images (step 76). This may be performed while step 72 continues and additional images of the first set are acquired. At this stage, acquiring of the second set of images (step 78) may commence, while one or more of steps 72, 74 and 76 are continued (or resumed). Alternatively, images belonging to the first and second sets may be acquired simultaneously and/or alternately with respect to one another (steps 72 and 78), prior to the analysis of the first set of images (step 74) commencing, or at the same time as the analysis of the first set of images is performed.

Once a second set of at least one image(s) has been acquired, in step 80, images belonging to the first and second sets of images are compared to one another, and in step 82, the computer processor determines a characteristic of the blood sample based at least in part upon the comparison of the first and second images to one another. Steps 80 and 82 are typically generally similar to steps 60 and 62 described with reference to FIG. 4. Optionally, comparing images of the first and second sets (step 80) commences, before steps 72, 74, 76 and/or 78 are completed.

Typically, in step 72, a set of two or more first images are acquired from respective fields of view. For example, as described hereinabove, the microscope system may scan a sample carrier and acquired a plurality of images of the sample carrier form respective fields of view. For some applications, in step 74 the computer processor analyzes one or more of the first set of images of the sample. In response thereto, the computer processor may acquire at least one second image (or recommend that a second image be acquired) from all of the fields of view in which there are entities that are platelet and/or intra-erythrocytic-entity (e.g., *Plasmodium*, and/or *Babesia*) candidates, or from only a portion of the fields of view in which there are entities that are platelet and/or *Plasmodium*, and/or *Babesia* candidates. If only a portion of the fields of view are re-imaged, then typically the results of the analysis of those fields of view are extrapolated and applied to fields of view in which there were entities that were platelet and/or *Plasmodium*, and/or *Babesia* candidates, but which were nor re-imaged. Typically, if the computer processor determines that a first image of a given portion of the sample should be re-imaged (e.g., because it contains entities as described herein), then a second image is acquired that at least partially overlaps with the first image. Typically, the area of overlap will include at least one erythrocyte, and at least one entity which is disposed in the vicinity of the erythrocyte, as described herein.

For some applications, in step 74, the computer processor runs an algorithm in order to determine whether some or all of the fields of view should be re-imaged, based upon an overall analysis of the first set of images. For example, the computer processor may take one or more of the following factors into account when determining whether to re-image (or recommend to re-image) all or a portion of a sample: the number of candidate *Plasmodium* parasites, and/or *Babesia* parasites, their associated parasitic phase, and/or the likelihood of false positive diagnosis of malaria due to platelet adhesion, and/or the likelihood of presence of specific types of blood cells or inclusion bodies found in such cells (e.g. reticulocytes, Howell Jolly Bodies, Heinz bodies, Pappenheimer bodies, and/or nucleated erythrocytes). For some applications, the likelihood of false positive diagnosis of malaria due to platelet adhesion is determined based upon the general platelet count in the sample, and/or the platelet morphology, and/or fluorescence of platelets within the sample that do not overlap with erythrocytes. For some applications, only images that contain platelet candidates that have morphology and/or fluorescence that are similar to that of platelets within the sample that do not overlap with erythrocytes are re-imaged (or recommended to be re-imaged).

For some applications, the computer processor determines that some or all of the fields of view should be re-imaged, in order to improve a parasitemia count, even though the computer processor has diagnosed the subject as having malaria.

Figure 6:
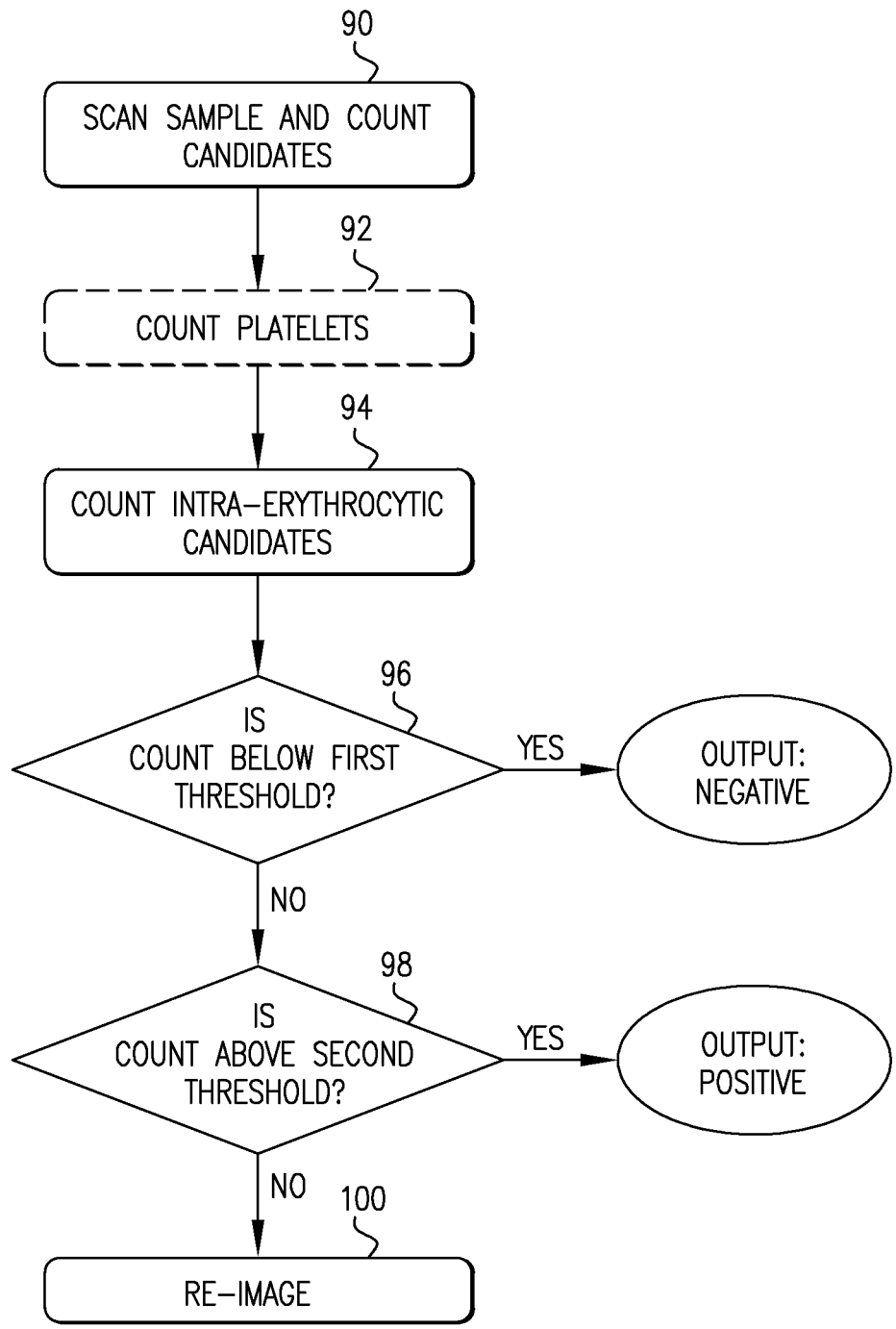
FIG. 6 is a flowchart showing steps of a procedure for analyzing a blood sample, in accordance with some applications of the present invention.

Reference is now made to FIG. 6, which is a flowchart showing steps of a procedure for analyzing a blood sample, in accordance with some applications of the present invention. In step 90 of the procedure, a blood sample is imaged, typically, from a plurality of fields of view, in accordance with the techniques described hereinabove. In step 92, which is optional (as indicated by the dashed lines), a platelet count is determined or estimated by analyzing the acquired images. Optionally, this count is restricted to free platelets that are not intra-erythrocytic candidates. In step 94, a count of intra-erythrocytic candidates is determined by analyzing the acquired images. For example, in this step, the computer processor may determine a count of entities that have characteristics that are indicative of the entities being intra-erythrocytic parasites, such as *Plasmodium*, and/or *Babesia*.

In step 96, the computer processor determines whether the count of intra-erythrocytic candidates is below a first threshold. In response to determining that the count is below the first threshold, the computer processor determines that the sample is negative with respect to the intra-erythrocytic entity that is being detected. In step 98, the computer processor determines whether the count of intra-erythrocytic candidates is above a second threshold. This second threshold may be predetermined or may be adjusted at least partially according to a platelet count performed in step 92. Typically, a high platelet count would increase the likelihood that an intra-erythrocytic candidate is in fact a platelet, and thus the threshold may increase. In response to determining that the count is above the second threshold, the computer processor determines that the sample is positive with respect to the intra-erythrocytic entity that is being detected. For some applications, steps 96 and 98 are performed in reverse order, or at the same time as one another.

If the processor determines that the count of intra-erythrocytic candidates is above a first threshold, but below the second threshold, this may indicate that it is desirable to image at least some of the sample a second time, in order to determine whether there are any entities such as those described hereinabove (such as platelets), which may otherwise have been mistakenly identified as intra-erythrocytic entities. Therefore, in response to such a determination, the computer processor proceeds to step 100 and re-images at least a portion of the sample. As described hereinabove, for some applications, only a portion of the sample (e.g., portions which include entities regarding which it is unclear whether they are intra-erythrocytic or extra-erythrocytic) is re-imaged.

For some applications, the platelet count that was determined in step 92 is used as an input in determining whether to re-image a portion of the sample. For example, a platelet count that is greater than a threshold amount may be indicative of a greater likelihood that platelets may otherwise have been mistakenly identified as intra-erythrocytic entities. For some applications, the platelet count relates only to free platelets, i.e., platelets that are not intra-erythrocytic candidates.

For some applications, the apparatus and methods described herein are used for the detection of an infection by a DNA-carrying pathogen. As such, at least a first dye stains at least the DNA, if present in the sample to thereby provide a first stained area indicative of the presence of the DNA carrying pathogen in the sample. The pathogen may be any infectious microorganism. In some embodiments, the pathogen is a eukaryotic pathogen. When referring to eukaryotic pathogen, in the context of the present disclosure, it is to be understood as encompassing one cell pathogens and multicellular pathogens but also fungi, such as yeast (e.g. *Candida*) and *Aspergillus*.

For some applications, the pathogen is a eukaryotic pathogen. In accordance with such applications, the pathogen may be a one cell pathogen, such as protozoa. This includes genital protozoa, e.g. *Trichomonas vaginalis*, nervous system protozoa, e.g. *Naegleria fowleri* fecal protozoa, e.g. *Giardia lamblia*, blood protozoa. For some applications, the pathogen may be a multicellular pathogen, such as *Wuchereria bancrofti, Brugia malayi, Brugia timori, Mansonella streptocerca*, or *Onchocerca volvulus*.

For some applications, the pathogen is a blood protozoa selected from the genuses consisting of *Trypanosoma* (causing Chagas disease and African sleeping sickness); *Plasmodium* (causing Malaria); *Toxoplasma* (causing Toxoplasmosis); *Babesia* (causing Babesiosis).

References to *Plasmodium* are to be understood as encompassing at least any member of the group consisting of *Plasmodium falciparum* (*P. falciparum*), *Plasmodium vivax* (*P. vivax*), *Plasmodium ovale* (*P. ovale*), *Plasmodium malariae* (*P. malariae*), and *Plasmodium knowlesi* (*P. knowlesi*).

References to *Babesia* are to be understood as encompassing at least any member of the group consisting of *Babesia duncani* (*B. duncani*) or *Babesia microti* (*B. microti*) and *Babesia divergens* (*B. divergens*).

It is noted that the terms "parasite" and "pathogen" are used interchangeably in the context of the present application. For some applications, the terms "pathogen" and "parasite" refer to a particular stage of the life cycle of a particular pathogen or group thereof. For example, the invention disclosed herein can be applied specifically to the detection of trophozoites, schizonts and/or gametocytes of *Plasmodium* species or *P. falciparum* in particular.

The apparatus and methods described herein may be applicable for the detection of multiple pathogens using the same conditions and/or in the same sample, e.g., the same combination of dyes, same test conditions, etc., as well as for the detection of a pathogen at multiple stages of its life cycle. For some applications, the apparatus and methods described herein may determine which one or more of the multiple pathogens (or life stages) is suspected.

Applications of the invention described herein can take the form of a computer program product accessible from a computer-usable or computer-readable medium (e.g., a non-transitory computer-readable medium) providing program code for use by or in connection with a computer or any instruction execution system, such as computer processor 28. For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-RAY) and DVD.

A data processing system suitable for storing and/or executing program code will include at least one processor (e.g., computer processor 28) coupled directly or indirectly to memory elements (e.g., memory 29) through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object oriented programming language such as Java, Smalltalk, C++ or the like and conventional procedural programming languages, such as the C programming language or similar programming languages.

It will be understood that blocks of the flowcharts shown in FIGS. 4-6 and combinations of blocks in the flowchart, can be implemented by computer program instructions. These computer program instructions may be provided to a processor of a general purpose computer, special purpose computer, or other programmable data processing apparatus to produce a machine, such that the instructions, which execute via the processor of the computer (e.g., computer processor 28) or other programmable data processing apparatus, create means for implementing the functions/acts specified in the flowcharts and/or algorithms described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the flowchart blocks and algorithms. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowcharts and/or algorithms described in the present application.

Computer processor 28 is typically a hardware device programmed with computer program instructions to produce a special purpose computer. For example, when programmed to perform the algorithms described with reference to FIGS. 4-6, computer processor 28 typically acts as a special purpose blood-sample-analysis computer processor. Typically, the operations described herein that are performed by computer processor 28 transform the physical state of memory 29, which is a real physical article, to have a different magnetic polarity, electrical charge, or the like depending on the technology of the memory that is used. For some applications, operations that are described as being performed by a computer processor are performed by a plurality of computer processors in combination with each other.

Typically, computer processor generates an output on output device 34. The output may be provided in any acceptable form, including a graph, graphic or text displayed on a monitor of a control unit, a printout, as a voice message, or on a user's smartphone display, for accepting processed data from the processing utility and displaying information relating to the structural features obtained and/or associated values determining the presence and optionally the identity of a pathogenic infection, using lists, tables, graphs etc. The output device may include a monitor that is connected to a printer for printing the output.

User interface 32 may be used to control the operation of system 10 and/or computer processor 28, including, inter alia, inputting data with respect to the examined bodily fluid source, date, place, etc.), controlling conditions of operating the system, types of dyes used, number of images to be taken, time interval between images, etc.

At times, image analysis by the computer processor may involve adjustment or normalization of image brightness on the basis of degree of staining of the sample. These may be based on, for example, identifying one or more of brightest and/or dimmest pixel values in the image or set of image (for example, corresponding to a particular sample), average brightness of brightest and/or dimmest area, and/or image histogram. Such features may be extracted from a representative image (not necessarily the one being normalized) or from statistical analysis of multiple images. The features used for normalization may be based on a single or multiple images, which may be captured using different excitation wavelengths (e.g., acridine orange providing different colors under different illumination wavelengths).

Image brightness may also be adjusted using other control means, such as image capturing component exposure time and/or brightness of illumination.

The conditions of microscope system 10 may be such as to control the timing of the image acquisition, e.g., to allow sufficient incubation time with the one or more dyes as well as the operation with different optical configurations of excitation and/or emission wavelengths, in order to image the stained sample at various colors or fluorescence spectra.

In order to image the stained sample at various colors or fluorescence spectra, changes in excitation may be achieved by switching the color of illumination. This can be done, for example, by providing two or more light sources (e.g. for acridine orange, UV LED light at 365 nm and blue LED light at 475 nm) and combining them optically (for example, using a dichroic mirror, or a grating).

In another example, a single illumination source (e.g., UV LED light at 365 nm) may be used to excite two dyes simultaneously, and one or more optical filters are moved in or out of the optical path to select the relevant emission wavelengths. Other dye sets can be simultaneously excited using the same incident illumination as described here, even if one or more of the dye is excited non-optimally. As an example, acridine orange can be similarly co-excited together with a Hoechst stain, DAPI and DRAQ stains.

In yet another example, a single illumination source (e.g. UV LED light at 365 nm) may be used to excite two or more dyes simultaneously, and the emission optical path is split such that the two or more emissions are captured on two or more image capturing components.

In yet another example, a color imaging sensor is used to simultaneously capture two or more fluorescence signals. Use of a color imaging sensor can, for example, obviate the need for one or more optical filters that are moved in or out of the optical path to select the relevant wavelength.

In the context of the present disclosure, various illumination sources may be used. These include, without being limited thereto, those providing white light (as in bright light microscopy), UV light, blue light, green light, yellow light, red light, a combination thereof, or any light applicable for exciting one or more of the dyes used for staining.

The components of the system, namely, imaging module 14, computer processor 28, output device 34, etc., may be directly connected to each other (e.g. directly by a wire) or one or more of the components may be remote from one or more other components. For example, the imaging module may send data to computer processor 28 over an intranet or over the internet, to allow processing at a remote location.

Examples of systems which may be used for performing the method of the present disclosure are described in WO 2012/090198 to Bachelet and in US 2014/0347459 to Greenfield, both of which applications are incorporated herein by reference. It is noted that, although with respect to some applications of the present invention, images of a sample are described as being acquired using a microscope system, the scope of the present invention includes using any imaging system for acquiring images of a sample, mutatis mutandis.

Figure 7:
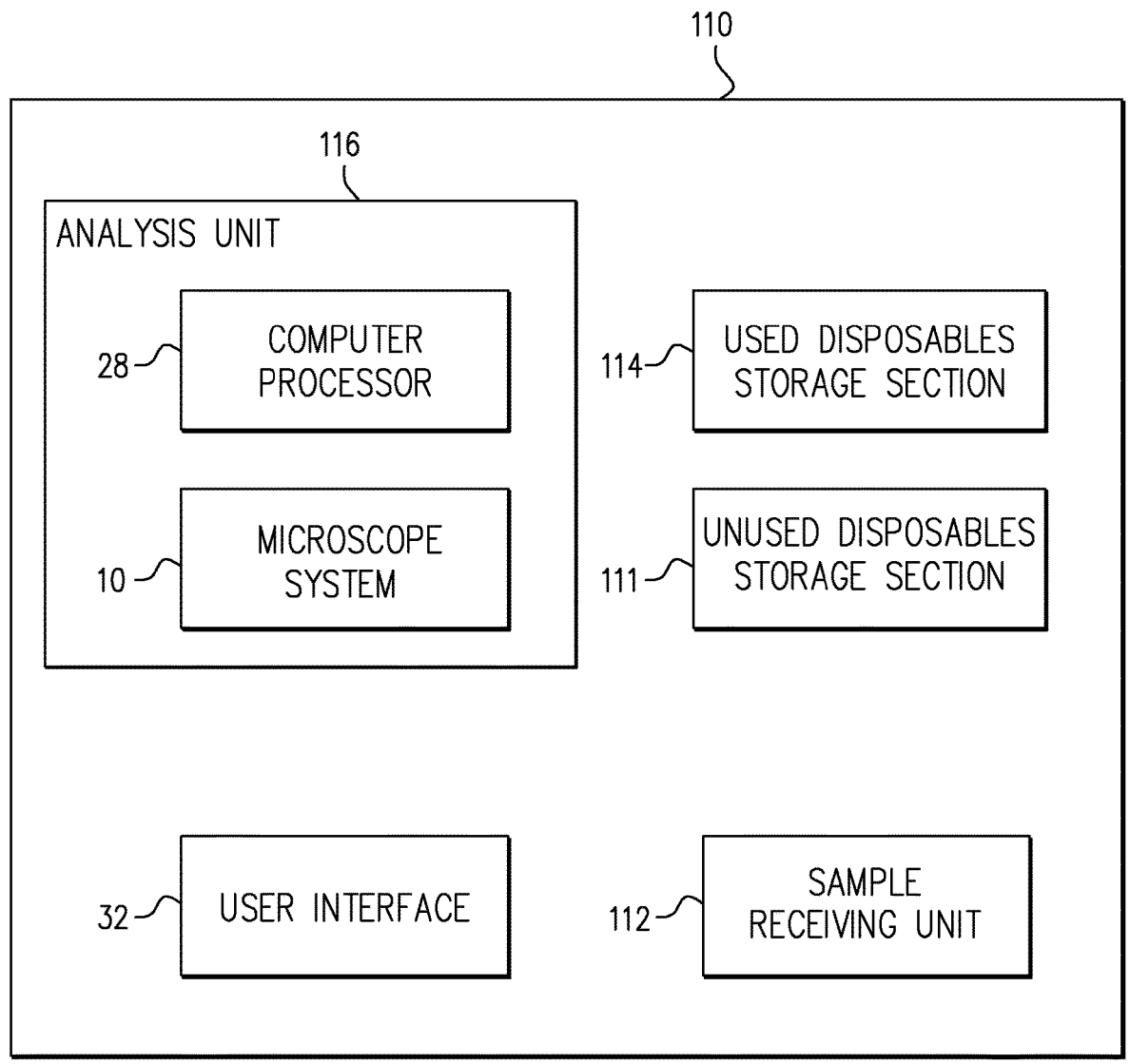
FIG. 7 is a schematic illustration of a blood diagnosis machine, in accordance with some applications of the present invention.

Reference is now made to FIG. 7, which is a schematic illustration of a blood diagnosis machine 110, in accordance with some applications of the present invention. For some applications, microscope system 10 is configured for use with blood diagnosis machine 110, the machine being an operator-free fully automated blood diagnosis machine which allows patients to undergo blood tests without the assistance of trained personnel in the extraction of the blood sample or operation of the device. The machine may be configured to perform any type of test which requires only a limited amount of blood. For example, these may include complete blood count, CD4 count, and/or or malaria tests. The machine may be placed in medical facilities or non-medical facilities (e.g., pharmacies). When placed at the facility, upon receiving a formal prescription or any other authorized form, and/or at will, the general public may come and undergo a blood test at his/her convenience without needing to set up an appointment.

For such applications, typically, before a test is performed, the user will identify himself/herself to machine 110, via user interface 32, which is typically as described hereinabove. The identification may be performed using a state issued identification (ID) card or number, a system username or card, a patient ID, insurance ID, biometric identification or any other accepted means of identification. The test to be performed is typically determined either by formal prescription or any other authorized form presented to the machine via user interface 32, or through a network connection to one or more medical service providers.

Once the user identification and tests are verified, a small amount of blood (typically, 20 microliters), is extracted from the user and placed into the machine. For example, the machine may provide the user with the required apparatus (e.g. a disposable lancet and capillary device), which are stored in an unused disposables storage section 111, and the user may then extract blood and place the blood into the machine, e.g., into a sample receiving unit 112 of the machine. Alternatively, the device itself may perform the sample extraction. For example, the user may place a finger into the device and the device automatically lancets and extracts the required amount of blood. The machine typically proceeds to automatically perform any necessary sample preparation, e.g., blood staining and injection into a cartridge, using disposables which are typically be stored in unused disposables storage section 111. Used disposables are typically transferred to a used disposables storage section 114. The sample is then automatically analyzed by an analysis unit 116, which typically includes microscope system 10, as well as computer processor 28, both of which are typically generally as described hereinabove. For example, fluorescent and/or bright-field microscope images may be acquired by microscope system 10. Based upon the analysis, the analysis unit evaluates relevant measurands. The analysis of the blood sample is typically completed within a short time, e.g. within 10 minutes.

Typically, once a test is completed, machine 110 notifies the user whether the test was performed successfully or not, via user interface 32, e.g., via an on-machine notification screen or through a phone or text message (e.g., via e-mail), or any other relevant means. Further typically, the device sends the results through secured means either directly to the prescribing doctor or to one or more central lab information systems, or any other authorized servers.

To facilitate servicing and maintenance, the machine typically communicates with an online server. Using this connection, data on machine status, such as usage statistics, failures, or internal inventory are accessed and software updates are performed. Furthermore, online support for users of the machine may also be provided through this or similar servers.

A blood sample as described herein may be from any living creature, and is typically from warm blooded animals. For some applications, the blood sample is a sample from a mammal, e.g., from a human body. For some applications, the sample is taken from any domestic animal, zoo animals and farm animals, including but not limited to dogs, cats, horses, cows and sheep. Alternatively or additionally, the blood sample is taken from animals that act as disease vectors including deer or rats.

There is provided, in accordance with some applications of the present invention, the following inventive concepts:
Inventive concept 1. A method for use with a blood sample that was drawn from a subject, the method comprising:
acquiring first and second images of the blood sample at respective times, using a microscope system; and using a computer processor:
  determining whether between acquisitions of the first and second images there was relative motion between at least one erythrocyte within the sample and at least one entity within the sample, by comparing the first and second images to one another;
  at least partially in response thereto, determining whether the entity is an extra-erythrocytic or an intra-erythrocytic entity; and
  generating an output, at least partially in response thereto.

Inventive concept 2. The method according to inventive concept 1, wherein the microscope system includes a microscope system that is disposed in a blood diagnosis machine that is accessible to the subject, and wherein the method comprises receiving the blood sample into the blood diagnosis machine by the subject placing the blood sample into a sample receiving unit of the blood diagnosis machine.

Inventive concept 3. The method according to inventive concept 1 or inventive concept 2, wherein acquiring first and second images of the blood sample comprises acquiring first and second at least partially overlapping images of a portion of the blood sample.

Inventive concept 4. The method according to any one of inventive concepts 1-3, wherein determining whether the entity is an extra-erythrocytic or an intra-erythrocytic entity comprises determining whether the entity is an extra-erythrocytic or an intra-erythrocytic entity, at least partially based upon an amount of motion between the erythrocyte and the entity, and a time interval between acquisitions of the first and second images.

Inventive concept 5. The method according to any one of inventive concepts 1-3, wherein determining whether the entity is an extra-erythrocytic or an intra-erythrocytic entity comprises determining whether the entity is an extra-erythrocytic or an intra-erythrocytic entity, at least partially based upon an amount of motion between the erythrocyte and the entity, and an amount of agitation applied to the blood sample between acquisitions of the first and second images.

Inventive concept 6. The method according to any one of inventive concepts 1-3, wherein determining whether the entity is an extra-erythrocytic or an intra-erythrocytic entity comprises determining whether the entity is an extra-erythrocytic or an intra-erythrocytic entity, at least partially based upon an amount of motion between the erythrocyte and the entity, a time interval between acquisitions of the first and second images, and an amount of agitation applied to the blood sample between acquisitions of the first and second images.

Inventive concept 7. The method according to any one of inventive concepts 1-6, wherein acquiring the first and second images of the blood sample at respective times comprises acquiring the first image of the blood sample during a first scan of the blood sample in which a plurality of images of the blood sample are acquired from respective fields of view, and acquiring the second image of the blood sample during a second scan of the blood sample in which a plurality of images of the blood sample are acquired from respective fields of view.

Inventive concept 8. The method according to any one of inventive concepts 1-7, further comprising preparing the blood sample in a monolayer, wherein acquiring the first and second images of the blood sample comprises acquiring first and second images of the blood sample, while the blood sample is disposed in the monolayer.

Inventive concept 9. The method according to any one of inventive concepts 1-8, further comprising, using the computer processor, at least partially based upon determining whether the entity is an extra-erythrocytic or an intra-erythrocytic entity, performing a blood count of the subject, wherein generating the output comprises generating an indication of the blood count.

Inventive concept 10. The method according to any one of inventive concepts 1-9, further comprising, using the computer processor, at least partially based upon determining whether the entity is an extra-erythrocytic or an intra-erythrocytic entity, diagnosing the subject as suffering from an intra-erythrocytic infection, wherein generating the output comprises generating an indication of the diagnosis.

Inventive concept 11. The method according to any one of inventive concepts 1-10, further comprising, using the computer processor, at least partially based upon determining whether the entity is an extra-erythrocytic or an intra-erythrocytic entity, diagnosing the subject as suffering from a medical condition, wherein generating the output comprises generating an indication of the diagnosis.

Inventive concept 12. The method according to any one of inventive concepts 1-11, further comprising staining the blood sample with a staining substance, wherein acquiring the first and second images comprises acquiring the first and second images of the blood sample, while the blood sample is in a stained state.

Inventive concept 13. The method according to any one of inventive concepts 1-12, further comprising, using the computer processor:
  analyzing the first image;
  based upon the analysis, identifying one or more entities within the first image that are disposed in a vicinity of the erythrocyte, and which have dimensions that indicate that the entities could be platelets; and
  in response thereto, selecting to perform the comparing of the first image and the second image to one another.

Inventive concept 14. The method according to any one of inventive concepts 1-13, wherein determining whether the entity is an extra-erythrocytic or an intra-erythrocytic entity comprises determining whether the entity is a platelet.

Inventive concept 15. The method according to any one of inventive concepts 1-13, wherein determining whether the entity is an extra-erythrocytic or an intra-erythrocytic entity comprises determining that the entity is an intra-erythrocytic entity selected from the group consisting of: a Howell Jolly body, a reticular network of ribosomal DNA, a Heinz body, a Pappenheimer body, and a nucleus of a nucleated erythrocyte.

Inventive concept 16. The method according to any one of inventive concepts 1-13, wherein determining whether the entity is an extra-erythrocytic or an intra-erythrocytic entity comprises determining that the entity is an intra-erythrocytic parasite.

Inventive concept 17. The method according to inventive concept 16, wherein determining that the entity is an intra-erythrocytic parasite comprises determining that the entity is an intra-erythrocytic parasite selected from the group consisting of a *Plasmodium* parasite, and a *Babesia* parasite.

Inventive concept 18. The method according to any one of inventive concepts 1-15, wherein:
  acquiring the first image of the blood sample comprises acquiring a first set of images of the blood sample that includes a plurality of images;
  acquiring the second image of the blood sample comprises acquiring a second set of images of the blood sample that includes one or more images; and comparing the first and second images to one another comprises comparing one or more of the images belonging to the first set of images to respective images belonging to the second set of images.

Inventive concept 19. The method according to inventive concept 18, wherein comparing one or more of the images belonging to the first set of images to respective images belonging to the second set of images comprises comparing only some of the first set of images to respective images belonging to the second set of images, the method further comprising determining a characteristic of all of the blood sample based on the comparison.

Inventive concept 20. The method according to inventive concept 18, wherein acquiring the second set of images comprises imaging a portion of the blood sample that is smaller than a portion of the blood sample that was imaged by acquiring the first set of images.

Inventive concept 21. The method according to inventive concept 20, further comprising:
  analyzing the first set of images; and
  based upon the analysis, selecting the portion of the blood sample to image in the second set of images.

Inventive concept 22. The method according to any one of inventive concepts 1-15, wherein acquiring the first and second images of the blood sample at respective times comprises acquiring the first and second images of the blood sample, a time interval between acquisitions of the first and second images being less than ten minutes.

Inventive concept 23. The method according to inventive concept 22, wherein acquiring the first and second images of the blood sample at respective times comprises acquiring the first and second images of the blood sample, the time interval between acquisitions of the first and second images being less than one minute.

Inventive concept 24. The method according to inventive concept 23, wherein acquiring the first and second images of the blood sample at respective times comprises acquiring the first and second images of the blood sample, the time interval between acquisitions of the first and second images being less than one second.

Inventive concept 25. The method according to any one of inventive concepts 1-15, further comprising agitating the blood sample between acquisitions of the first and second images.

Inventive concept 26. The method according to inventive concept 25, wherein agitating the blood sample comprises placing magnetic beads inside the sample and moving the magnetic beads using an external magnetic field.

Inventive concept 27. The method according to inventive concept 25, wherein agitating the blood sample comprises moving a microscope stage upon which the blood sample is disposed.

Inventive concept 28. A method for use with a blood sample that was drawn from a subject, the method comprising:
  acquiring a first image of the blood sample, using a microscope system;
  acquiring a second image of the blood sample, using the microscope system, there being a time interval between acquisitions of the first and second images; and
  using a computer processor:
  analyzing the first image of the blood sample;
  at least partially in response thereto:
    selecting to compare the first and second images of the blood sample to one another;
    comparing the first and second images of the blood sample to one another; and
    determining a characteristic of the blood sample, at least partially based upon comparing the first and second images of the blood sample to one another; and
  generating an output in response to the determined characteristic.

Inventive concept 29. The method according to inventive concept 28, wherein the microscope system includes a microscope system that is disposed in a blood diagnosis machine that is accessible to the subject, and wherein the method comprises receiving the blood sample into the blood diagnosis machine by the subject placing the blood sample into a sample receiving unit of the blood diagnosis machine.

Inventive concept 30. The method according to inventive concept 28 or inventive concept 29, wherein selecting to compare the first and second images of the blood sample to one another comprises selecting to acquire the second image of the blood sample, and wherein acquiring the second image of the blood sample comprises automatically acquiring the second image in response thereto.

Inventive concept 31. The method according to any one of inventive concepts 28-30, wherein acquiring the first and second images of the blood sample comprises acquiring the first image of the blood sample during a first scan of the blood sample in which a plurality of images of the blood sample are acquired from respective fields of view, and acquiring the second image of the blood sample during a second scan of the blood sample in which a plurality of images of the blood sample are acquired from respective fields of view.

Inventive concept 32. The method according to any one of inventive concepts 28-31, further comprising preparing the blood sample in a monolayer, wherein acquiring the first and second images of the blood sample comprises acquiring the first and second images of the blood sample, while the blood sample is disposed in the monolayer.

Inventive concept 33. The method according to any one of inventive concepts 28-32, further comprising staining the blood sample with a staining substance, wherein acquiring the first and second images of the blood sample comprises acquiring the first and second images of the blood sample while the blood sample is in a stained state.

Inventive concept 34. The method according to any one of inventive concepts 28-33, wherein:
  analyzing the first image comprises identifying one or more entities within the first image that are disposed in a vicinity of an erythrocyte, and which have dimensions that indicate that the entities could be platelets, and
  selecting to compare the first and second images of the blood sample to one another is performed at least partially in response thereto.

Inventive concept 35. The method according to any one of inventive concepts 28-34, wherein:
  acquiring the first image of the blood sample comprises acquiring a first set of images of the blood sample that includes a plurality of images;
  acquiring the second image of the blood sample comprises acquiring a second set of images of the blood sample that includes one or more images; and
  selecting to compare the first and second images of the blood sample to one another comprises selecting to compare at least a portion of the images belonging to the plurality of first images to respective images belonging to the plurality of second images.

Inventive concept 36. The method according to inventive concept 35, wherein selecting to compare at least a portion of the images belonging to the plurality of first images to respective images belonging to the plurality of second images comprises selecting to compare only some of the plurality of first images to respective images belonging to the plurality of second images, the method further comprising determining a characteristic of all of the blood sample based on comparing only some of the plurality of first images to respective images belonging to the plurality of second images.

Inventive concept 37. The method according to inventive concept 35, wherein selecting to compare the first and second images of the blood sample to one another comprises selecting to acquire the second set of images of the blood sample, the second set of images imaging a portion of the blood sample that is smaller than a portion of the blood sample that was imaged by acquiring the first set of images.

Inventive concept 38. The method according to any one of inventive concepts 28-34, wherein determining a characteristic of the blood sample, at least partially based upon comparing the first and second images to one another comprises:
  determining whether between acquisitions of the first and second images, there was relative motion between at least one erythrocyte within the sample and at least one entity within the sample; and
  at least partially in response thereto, determining whether the entity is an extra-erythrocytic or an intra-erythrocytic entity.

Inventive concept 39. The method according to inventive concept 38, wherein determining whether the entity is an extra-erythrocytic or an intra-erythrocytic entity comprises determining whether the entity is an extra-erythrocytic or an intra-erythrocytic entity, at least partially based upon an amount of motion between the erythrocyte and the entity, and the time interval between acquisitions of the first and second images.

Inventive concept 40. The method according to inventive concept 38, wherein determining whether the entity is an extra-erythrocytic or an intra-erythrocytic entity comprises determining whether the entity is an extra-erythrocytic or an intra-erythrocytic entity, at least partially based upon an amount of motion between the erythrocyte and the entity, and an amount of agitation applied to the blood sample between acquisitions of the first and second images.

Inventive concept 41. The method according to inventive concept 38, wherein determining whether the entity is an extra-erythrocytic or an intra-erythrocytic entity comprises determining whether the entity is an extra-erythrocytic or an intra-erythrocytic entity, at least partially based upon an amount of motion between the erythrocyte and the entity, the time interval between acquisitions of the first and second images, and an amount of agitation applied to the blood sample between acquisitions of the first and second images.

Inventive concept 42. The method according to inventive concept 38, further comprising, using the computer processor, at least partially based upon determining whether the entity is an extra-erythrocytic or an intra-erythrocytic entity, performing a blood count of the subject, wherein generating the output comprises generating an indication of the blood count.

Inventive concept 43. The method according to inventive concept 38, further comprising, using the computer processor, at least partially based upon determining whether the entity is an extra-erythrocytic or an intra-erythrocytic entity, diagnosing the subject as suffering from an intra-erythrocytic infection, wherein generating the output comprises generating an indication of the diagnosis.

Inventive concept 44. The method according to inventive concept 38, further comprising, using the computer processor, at least partially based upon determining whether the entity is an extra-erythrocytic or an intra-erythrocytic entity, diagnosing the subject as suffering from a medical condition, wherein generating the output comprises generating an indication of the diagnosis.

Inventive concept 45. The method according to inventive concept 38, wherein determining whether the entity is an extra-erythrocytic or an intra-erythrocytic entity comprises determining that the entity is a platelet.

Inventive concept 46. The method according to inventive concept 38, wherein determining whether the entity is an extra-erythrocytic or an intra-erythrocytic entity comprises determining that the entity is an intra-erythrocytic entity selected from the group consisting of: a Howell Jolly body, a reticular network of ribosomal DNA, a Heinz body, a Pappenheimer body, and a nucleus of a nucleated erythrocyte.

Inventive concept 47. The method according to inventive concept 38, wherein determining whether the entity is an extra-erythrocytic or an intra-erythrocytic entity comprises determining that the entity is an intra-erythrocytic parasite.

Inventive concept 48. The method according to inventive concept 47, wherein determining that the entity is an intra-erythrocytic parasite comprises determining that the entity is an intra-erythrocytic parasite selected from the group consisting of a *Plasmodium* parasite, and a *Babesia* parasite.

Inventive concept 49. The method according to any one of inventive concepts 28-34, wherein acquiring the first and second images of the blood sample comprises acquiring the first and second images of the blood sample, the time interval between acquisitions of the first and second images being less than ten minutes.

Inventive concept 50. The method according to inventive concept 49, wherein acquiring the first and second images of the blood sample comprises acquiring the first and second images of the blood sample, the time interval between acquisitions of the first and second images being less than one minute.

Inventive concept 51. The method according to inventive concept 50, wherein acquiring the first and second images of the blood sample comprises acquiring the first and second images of the blood sample, the time interval between acquisitions of the first and second images being less than one second.

Inventive concept 52. The method according to any one of inventive concepts 28-34, further comprising agitating the blood sample between acquisitions of the first and second images.

Inventive concept 53. The method according to inventive concept 52, wherein agitating the blood sample comprises placing magnetic beads inside the sample and moving the magnetic beads using an external magnetic field.

Inventive concept 54. The method according to inventive concept 52, wherein agitating the blood sample comprises moving a microscope stage upon which the blood sample is disposed.

Inventive concept 55. A computer software product, for use with a blood sample that was drawn from a subject, and a microscope system configured to acquire first and second images of the blood sample at respective times, the computer software product comprising a non-transitory computer-readable medium in which program instructions are stored, which instructions, when read by a computer cause the computer to perform the steps of: determining whether between acquisitions of the first and second images there was relative motion between at least one erythrocyte within the sample and at least one entity within the sample, by comparing the first and second images to one another; at least partially in response thereto, determining whether the entity is an extra-erythrocytic or an intra-erythrocytic entity; and generating an output, at least partially in response thereto.

Inventive concept 56. A computer software product, for use with a blood sample that was drawn from a subject, and a microscope system configured to acquire a first and image of the blood sample and a second image of the blood sample, there being a time interval between acquisitions of the first and second images, the computer software product comprising a non-transitory computer-readable medium in which program instructions are stored, which instructions, when read by a computer cause the computer to perform the steps of: analyzing the first image of the blood sample; at least partially in response thereto: selecting to compare the first and second images of the blood sample to one another; comparing the first and second images of the blood sample to one another; and determining a characteristic of the blood sample, at least partially based upon comparing the first and second images of the blood sample to one another; and generating an output in response to the determined characteristic.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a blood sample that was drawn from a subject and an output device, the apparatus comprising:
   a microscope system configured to acquire:
      a first image of the blood sample, using a microscope system, and
      a second image of the blood sample, there being a time interval between acquisitions of the first and second images; and
   a computer processor configured to:
      analyze the first image of the blood sample, and
      only in response to determining by the analysis of the first image that there are one or more entities within the image that may be either an extra-erythrocytic entity or an intra-erythrocytic entity:
         select to compare the first and second images of the blood sample to one another,
         compare the first and second images of the blood sample to one another, and
         determine a characteristic of the blood sample, at least partially based upon comparing the first and second images of the blood sample to one another by:
            determining whether between acquisitions of the first and second images, there was relative motion between at least one erythrocyte within the sample and at least one entity within the sample; and
            at least partially in response thereto, determining whether the entity is an extra-erythrocytic or an intra-erythrocytic entity, and generate an output in response to the determined characteristic.

2. The apparatus according to claim 1, wherein the microscope system includes a microscope system that is disposed in a blood diagnosis machine, the apparatus further comprising a sample receiving unit configured to receive the blood sample into the blood diagnosis machine by the subject placing the blood sample into the sample receiving unit.

3. The apparatus according to claim 1, wherein the computer processor, in selecting to compare the first and second images of the blood sample to one another, is configured to select to acquire the second image of the blood sample, and is configured to automatically drive the microscope system to acquire the second image, in response thereto.

4. The apparatus according to claim 1, wherein the microscope system is configured to acquire the first and second images of the blood sample by acquiring the first image of the blood sample during a first scan of the blood sample in which a plurality of images of the blood sample are acquired from respective fields of view, and acquiring the second image of the blood sample during a second scan of the blood sample in which a plurality of images of the blood sample are acquired from respective fields of view.

5. The apparatus according to claim 1, further comprising a staining substance configured to stain the blood sample, wherein the microscope system is configured to acquire the first and second images by acquiring the first and second images of the blood sample, while the blood sample is in a stained state.

6. The apparatus according to claim 1, wherein the computer processor is configured:
   to identify one or more entities within the first image that are disposed in a vicinity of the erythrocyte, and which have dimensions that indicate that the entities could be platelets, by analyzing the first image, and
   to select to compare the first and second images of the blood sample to one another in response thereto.

7. The apparatus according to claim 1, wherein:
   the microscope system is configured to acquire the first image of the blood sample by acquiring a first set of images of the blood sample that includes a plurality of images;
   the microscope system is configured to acquire the second image of the blood sample by acquiring a second set of images of the blood sample that includes a plurality of images; and
   the computer processor is configured to select to compare at least a portion of the images belonging to the plurality of first images to respective images belonging to the plurality of second images.

8. The apparatus according to claim 7, wherein the computer processor is configured to select to compare only some of the plurality of first images to respective images belonging to the plurality of second images, and is configured to determine a characteristic of all of the blood sample based on comparing only some of the plurality of first images to respective images belonging to the plurality of second images.

9. The apparatus according to claim 7, wherein the computer processor, in selecting to compare the first and second images of the blood sample to one another, is configured to select to acquire the second set of images of the blood sample, the second set of images imaging a portion of the blood sample that is smaller than a portion of the blood sample that was imaged by acquiring the first set of images.

10. The apparatus according to claim 1, wherein the computer processor is configured to determine whether the entity is an extra-erythrocytic or an intra-erythrocytic entity, at least partially based upon an amount of motion between the erythrocyte and the entity, and the time interval between acquisitions of the first and second images.

11. The apparatus according to claim 1, wherein the computer processor is configured to determine whether the entity is an extra-erythrocytic or an intra- erythrocytic entity, at least partially based upon an amount of motion between the erythrocyte and the entity, and an amount of agitation applied to the blood sample between acquisitions of the first and second images.

12. The apparatus according to claim 1, wherein the computer processor is configured to determine whether the entity is an extra-erythrocytic or an intra- erythrocytic entity, at least partially based upon an amount of motion between the erythrocyte and the entity, the time interval between acquisitions of the first and second images, and an amount of agitation applied to the blood sample between acquisitions of the first and second images.

13. The apparatus according to claim 1, wherein the computer processor is configured to perform a blood count of the subject, at least partially based upon determining whether the entity is an extra-erythrocytic or an intra-erythrocytic entity, and the computer processor is configured to generate the output by generating an indication of the blood count.

14. The apparatus according to claim 1, wherein the computer processor is configured to diagnose the subject as suffering from an intra-erythrocytic infection, at least partially based upon determining whether the entity is an extra-erythrocytic or an intra- erythrocytic entity, and the computer processor is configured to generate the output by generating an indication of the diagnosis.

15. The apparatus according to claim 1, wherein the computer processor is configured to diagnose the subject as suffering from a medical condition, at least partially based upon determining whether the entity is an extra-erythrocytic or an intra- erythrocytic entity, and the computer processor is configured to generate the output by generating an indication of the diagnosis.

16. The apparatus according to claim 1, wherein the computer processor is configured to determine whether the entity is a platelet, at least partially based upon determining whether the entity is an extra-erythrocytic or an intra-erythrocytic entity.

17. The apparatus according to claim 1, wherein the computer processor is configured to determine whether the entity is an intra-erythrocytic entity selected from the group consisting of: a Howell Jolly body, a reticular network of ribosomal DNA, a Heinz body, a Pappenheimer body, and a nucleus of a nucleated erythrocyte, at least partially based upon determining whether the entity is an extra-erythrocytic or an intra-erythrocytic entity.

18. The apparatus according to claim 1, wherein the computer processor is configured to determine whether the entity is an intra-erythrocytic parasite, at least partially based upon determining whether the entity is an extra-erythrocytic or an intra- erythrocytic entity.

19. The apparatus according to claim 18, wherein the computer processor is configured to determine that the entity is an intra-erythrocytic parasite selected from the group consisting of a Plasmodium parasite, and a Babesia parasite, at least partially based upon determining whether the entity is an extra-erythrocytic or an intra-erythrocytic entity.

20. A method for use with a blood sample that was drawn from a subject, the method comprising:
  using a microscope system, acquiring:
    a first image of the blood sample, using a microscope system, and
    a second image of the blood sample, there being a time interval between acquisitions of the first and second images; and
  using a computer processor:
    analyzing the first image of the blood sample,
    only in response to determining by the analysis of the first image that there are one or more entities within the image that may be either an extra-erythrocytic entity or an intra-erythrocytic entity:
      selecting to compare the first and second images of the blood sample to one another,
      comparing the first and second images of the blood sample to one another, and
      determining a characteristic of the blood sample, at least partially based upon comparing the first and second images of the blood sample to one another, by determining whether between acquisitions of the first and second images, there was relative motion between at least one erythrocyte within the sample and at least one entity within the sample; and
    at least partially in response thereto, determining whether the entity is an extra-erythrocytic or an intra-erythrocytic entity, and
    generating an output on an output device, in response to the determined characteristic.

21. The method according to claim 20, wherein determining whether the entity is an extra-erythrocytic or an intra-erythrocytic entity, is at least partially based upon an amount of motion between the erythrocyte and the entity, and the time interval between acquisitions of the first and second images.

22. The method according to claim 20, further comprising using the computer processor, performing a blood count of the subject, at least partially based upon determining whether the entity is an extra-erythrocytic or an intra-erythrocytic entity, and wherein generating the output, comprises generating an indication of the blood count.

23. The method according to claim 20, further comprising using the computer processor, diagnosing the subject as suffering from an intra-erythrocytic infection, at least partially based upon determining whether the entity is an extra-erythrocytic or an intra- erythrocytic entity, and wherein generating the output comprises generating an indication of the diagnosis.

24. The method according to claim 20, further comprising using the computer processor diagnosing the subject as suffering from a medical condition, at least partially based upon determining whether the entity is an extra-erythrocytic or an intra- erythrocytic entity, and wherein generating the output comprises generating an indication of the diagnosis.

25. The method according to claim 20, wherein determining a characteristic of the blood sample comprises determining whether the entity is a platelet, at least partially based upon determining whether the entity is an extra-erythrocytic or an intra- erythrocytic entity.

26. The method according to claim 20, wherein determining whether the entity is an extra-erythrocytic or an intra-erythrocytic entity comprises determining whether the intra-erythrocytic entity is an intra-erythrocytic entity selected from the group consisting of: a Howell Jolly body, a reticular network of ribosomal DNA, a Heinz body, a Pappenheimer body, and a nucleus of a nucleated erythrocyte, at least partially based upon determining whether the entity is an extra-erythrocytic or an intra-erythrocytic entity.

27. The method according to claim 20, further comprising determining whether the entity is an intra-erythrocytic parasite, at least partially based upon determining whether the entity is an extra-erythrocytic or an intra-erythrocytic entity.

28. The method according to claim 27, wherein determining whether the entity is an intra-erythrocytic parasite comprises determining whether the entity is an intra-erythrocytic parasite selected from the group consisting of a Plasmodium parasite, and a Babesia parasite, at least partially based upon determining whether the entity is an extra- erythrocytic or an intra-erythrocytic entity.

* * * * *